US00RE48181E

(19) United States
(12) Reissued Patent
Trollsas et al.

(10) Patent Number: US RE48,181 E
(45) Date of Reissued Patent: Sep. 1, 2020

(54) CAPSULE DEVICE HAVING VARIABLE SPECIFIC GRAVITY

(71) Applicant: CapsoVision, Inc., Saratoga, CA (US)

(72) Inventors: Mikael Trollsas, San Jose, CA (US); Phat Trinh, San Jose, CA (US); Mark Hadley, Newark, CA (US); Kang-Huai Wang, Saratoga, CA (US); Gordon Cook Wilson, San Francisco, CA (US); Ganyu Lu, Palo Alto, CA (US)

(73) Assignee: CAPSOVISION INC, Saratoga, CA (US)

(21) Appl. No.: 16/233,134

(22) Filed: Dec. 27, 2018

Related U.S. Patent Documents

Reissue of:
(64) Patent No.: 10,098,526
Issued: Oct. 16, 2018
Appl. No.: 14/659,832
Filed: Mar. 17, 2015

(51) Int. Cl.

| | |
|---|---|
| ***A61B 1/00*** | (2006.01) |
| ***A61B 1/04*** | (2006.01) |
| ***A61B 1/273*** | (2006.01) |
| ***A61B 5/145*** | (2006.01) |
| ***A61B 5/00*** | (2006.01) |
| ***A61B 5/07*** | (2006.01) |

(52) U.S. Cl.
CPC ..... *A61B 1/041* (2013.01); *A61B 1/00082* (2013.01); *A61B 1/00147* (2013.01); *A61B 1/2736* (2013.01); *A61B 5/073* (2013.01); *A61B 5/14539* (2013.01); *A61B 5/6861* (2013.01)

(58) Field of Classification Search
CPC ..... A61B 1/041
USPC ..... 600/114–117, 160, 164, 170, 171
See application file for complete search history.

(56) References Cited

U.S. PATENT DOCUMENTS

| | | | | |
|---|---|---|---|---|
| 8,580,853 | B2 * | 11/2013 | Phykitt | A61K 31/616 514/553 |
| 2002/0143237 | A1 * | 10/2002 | Oneda | A61B 1/00082 600/116 |
| 2002/0198439 | A1 * | 12/2002 | Mizuno | A61B 1/041 600/109 |
| 2003/0018280 | A1 * | 1/2003 | Lewkowicz | A61B 1/00082 600/549 |
| 2005/0058701 | A1 | 3/2005 | Gross et al. | |
| 2006/0058829 | A1 | 3/2006 | Sampson et al. | |

(Continued)

FOREIGN PATENT DOCUMENTS

| | | | |
|---|---|---|---|
| WO | 02/095351 | A2 | 11/2002 |
| WO | 2015/060814 | A1 | 4/2015 |

OTHER PUBLICATIONS

E-Z-Gas® II Effervescent Granules Antiacid/Antiflatulent, [retrieved from internet on Oct. 4, 2019 at https://dailymed.nlm.nih.gov/dailymed/fda/fdaDrugXsl.cfm?setid=4e12e1cb-b033-076d-e054-00144ff8d46c&type=display].*

*Primary Examiner* — Beverly M Flanagan
(74) *Attorney, Agent, or Firm* — B;airtech Solution LLC

(57) ABSTRACT

An endoscopy capsule having an image collecting capacity includes a deformable member configured to inflate when exposed to body liquid. The deformable member includes an effervescent material. When the effervescent reacts with water the resulting Carbon-Dioxide gas reduces the specific gravity of the endoscopy capsule. The capsule is contained within a shell or dome when swallowed. The shell or dome is configured dissolve in either a low or high pH environment.

27 Claims, 22 Drawing Sheets

(56) References Cited

U.S. PATENT DOCUMENTS

| | | | | |
|---|---|---|---|---|
| 2007/0100208 | A1* | 5/2007 | Lewkowicz | A61B 1/00082 600/160 |
| 2007/0282164 | A1* | 12/2007 | Frisch | A61B 1/00105 600/109 |
| 2008/0161702 | A1* | 7/2008 | Chang | A61B 1/00082 600/508 |
| 2008/0194912 | A1* | 8/2008 | Trovato | A61B 1/00055 600/118 |

* cited by examiner

| Material | Thickness | Size | Effervescent | Temperature | Grinding | Aging | Desiccant | Rise time | | Last time | | | | Comment |
|---|---|---|---|---|---|---|---|---|---|---|---|---|---|---|
| | | | | | | | | Ta | Tb | Tc | Td | Te | Tf | |
| | | | | | | | | 80% | 100% | | 100% | | 80% | |
| Thermoplastic Polyurethane Elastomer | 1mils | 30x10mm | 15mg | 37°C | Coarse | Aged | None | 0.5 | 0.7 | 0.9 | 0.2 | 1.3 | 0.8 | |
| | | | | | | | | 0.9 | 1.5 | 2 | 0.5 | 2.5 | 1.6 | |
| | | | | | | | | 0.4 | 0.6 | 0.8 | 0.2 | 1.3 | 0.9 | |
| | | | | | | | | 0.5 | 0.8 | 1.1 | 0.3 | 1.4 | 0.9 | |
| | 2mils | | | | | | | 0.7 | 1.2 | 1.5 | 0.3 | 2.1 | 1.4 | |
| | | | | | | | | 1 | 1.4 | 1.7 | 0.3 | 2.6 | 1.6 | |
| | 4mils | | | | | | | 1.3 | 2.3 | 2.7 | 0.4 | 4.5 | 3.2 | |
| | | | | | | | | 1.4 | 2.1 | 3 | 0.9 | 4.5 | 3.1 | |
| Polyether block Amide Copolymer | 1mils | 30x10mm | 15mg | 37°C | Coarse | Aged | None | 1 | 1.5 | 2.9 | 1.4 | 2.5 | 1.5 | |
| | | | | | | | | 1.2 | 1.6 | 1.8 | 0.2 | 2.4 | 1.2 | |
| | 2mils | | | | | | | 1.1 | 1.4 | 2.6 | 1.2 | 3.9 | 2.8 | |
| | | | | | | | | 0.9 | 1.3 | 1.6 | 0.3 | 2.4 | 1.5 | |
| | | | | | | | | 1.1 | 1.7 | 2.3 | 0.6 | 3.2 | 2.1 | |
| | | | | | | | | 1 | 1.8 | 2.3 | 0.5 | 3.4 | 2.4 | |
| | 4mils | | | | | | | 2 | 3.8 | 5 | 1.2 | 8 | 6 | |
| | | | | | | | | 2.4 | 4.5 | 4.9 | 0.4 | 6.7 | 4.3 | |
| | | | | | | | | 2 | 2.8 | 3.6 | 0.8 | 5.6 | 3.6 | |
| | | | | | | | | 1.6 | 2.5 | 3.3 | 0.8 | 4.8 | 3.2 | |
| Thermoplastic Polyurethane Elastomer | 1mils | 30x10mm | 20mg | 37°C | Coarse | Aged | None | 0.7 | 1.1 | 1.5 | 0.4 | 2.3 | 1.6 | |
| | | | | | | | | 1 | 1.4 | 1.7 | 0.3 | 2.4 | 1.4 | |
| | 4mils | | | | | | | 4.3 | 6.6 | 8.6 | 2 | 11.1 | 6.8 | |
| | | | | | | | | 4.5 | 6.2 | 7.7 | 1.5 | 12 | 7.5 | |

FIG. 7A

| | | | | | | | | | | | | | | |
|---|---|---|---|---|---|---|---|---|---|---|---|---|---|---|
| Polyether block Amide Copolymer | 1mils | 30x10mm | 20mg | 37°C | Coarse | Aged | None | 0.8 | 1.4 | 1.8 | 0.4 | 3 | 2.2 | |
| | | | | | | | | 1 | 1.6 | 2 | 0.4 | 3.2 | 2.2 | |
| | 4mils | 30x10mm | 20mg | 37°C | Coarse | Aged | None | 2.4 | 4 | 5.8 | 1.8 | 8.7 | 6.3 | |
| | | | | | | | | 2.4 | 3.9 | 6 | 2.1 | 8.4 | 6 | |
| | | | | | | Fresh | None | 1.2 | 2.1 | 2.9 | 0.8 | 6.3 | 5.1 | |
| | | | | | | | | 1 | 2.2 | 3 | 0.8 | 6 | 5 | |
| | | | | | | | | 1.3 | 2.1 | 4.1 | 2 | 7 | 5.7 | |
| | | | | | | | | 1.3 | 2.6 | 3.8 | 1.2 | 6.9 | 5.6 | |
| | | | | | Coarse | Fresh | None | 1.2 | 2.3 | 5.1 | 2.8 | 9.9 | 8.7 | |
| | | | | | | | | 1.3 | 2.6 | 3.4 | 0.8 | 7.4 | 6.1 | |
| | | | | | Fine | Fresh | None | 1.2 | 2.6 | 4 | 1.4 | 11.5 | 10.3 | |
| | | | | | | | | 1.2 | 2.8 | 4.6 | 1.8 | 11.4 | 10.2 | |
| | | | | | | | | 1 | 2 | 4.3 | 2.3 | 9.4 | 8.4 | |
| | | | | | | | | 1 | 2.4 | 5 | 2.6 | 10.4 | 9.4 | |
| | | | | | Fine | Aged | None | 2 | 3.2 | 5 | 1.8 | 8.4 | 6.4 | |
| | | | | | | | | 2 | 3.2 | 5 | 1.8 | 8.4 | 6.4 | |
| | | | | | | | | | | | | | | |
| | | | | | | | | | | | | | | |
| Polyether block Amide Copolymer | | | | | | | NaCl (20mg) | 1.6 | 2.8 | 3.4 | 0.6 | 8.5 | 6.9 | |
| | | | | | | | | 1.4 | 2.5 | 4.3 | 1.8 | 9.5 | 8.1 | |
| | | | | | | | PEG (10mg) | 1.4 | 3.5 | 4 | 0.5 | 9.4 | 8 | |
| | | | | | | | | 1.7 | 3.6 | 4.2 | 0.6 | 9.4 | 7.7 | |
| | | | | | | | PEG (20mg) | 2.1 | 3.7 | 5 | 1.3 | 8.9 | 6.8 | |
| | | | | | | | | 2.3 | 3.7 | 4.9 | 1.2 | 9.1 | 6.8 | |
| | | | | | | | PEG | 2.4 | 3.8 | 5 | 1.2 | 9.5 | 7.1 | |

FIG. 7A (Cont. 1)

| Material | Thickness | Size | Effervescent | Temperature | Grinding | Aging | Desiccant | Rise time | | Last time | | | | Comment |
|---|---|---|---|---|---|---|---|---|---|---|---|---|---|---|
| | | | | | | | | Ta | Tb | Tc | Td | Te | Tf | |
| | | | | | | | | 80% | 100% | | 100% | | 80% | |
| | 4mils | 30x10mm | 20mg | 37°C | Fine | Fresh | (30mg) | 2.3 | 3.9 | 5.9 | 2 | 11.2 | 8.9 | |
| | | | | | | | CaSo4 (20mg) | 2.7 | 3.9 | 4.7 | 0.8 | 9.2 | 6.5 | |
| | | | | | | | | 2.7 | 3.9 | 4.5 | 0.6 | 8.4 | 5.7 | |
| | | | | | | | Polyacrylic Acid Sodium Salt (20mg) | 17.3 | 19.8 | 21.3 | 1.5 | 26 | 8.7 | |
| | | | | | | | | 20 | 22 | 23 | 1 | 28.2 | 8.2 | |
| | | | | | | | CaO2 (20mg) | 1.1 | 1.6 | 1.8 | 0.2 | 2.2 | 1.1 | |
| | | | | | | | | 1.4 | 2.1 | 2.5 | 0.4 | 4 | 2.6 | |
| | | | | | | | CaCl2 (20mg) | 7 | 9.1 | 10.9 | 1.8 | 11.6 | 4.6 | |
| | | | | | | | | 0 | 0 | 0 | 0 | 0 | 0 | |
| | | | | | | | | | | | | | | |
| Polyamide 6.6 | 0.03mm | 2x1cm | 25mg | 37°C | Fine | Fresh | None | 0.2 | 0.3 | 0.6 | 0.3 | 2.8 | 2.6 | |
| | | | | | | | | 0.3 | 0.6 | 0.8 | 0.2 | 3 | 2.7 | |
| | | | | | | 4 Months | None | 0.9 | 2.4 | 2.5 | 0.1 | 4.5 | 3.6 | |
| | | | | | | | | 0.9 | 3.5 | 4 | 0.5 | 6.2 | 5.3 | |
| | | | | | | | | | | | | | | |
| Polyamide 6.6 | | 2x1cm | 5mg | 37°C | | | | 0.3 | 1 | 2.5 | 1.5 | 3.4 | 3.1 | |
| | | | | | | | | 0.16 | 0.6 | 2.5 | 1.9 | 3.4 | 3.24 | |
| | | | | | | | | 0.3 | 1.6 | 2.5 | 0.9 | 3.2 | 2.9 | |
| | | | | | | | | 0.1 | 0.6 | 2.5 | 1.9 | 3.2 | 3.1 | |
| | | | | | | | | 0.16 | 0.6 | 2.5 | 1.9 | 4 | 3.84 | |
| | | | 10mg | | | | | 0.2 | 0.3 | 1.1 | 0.8 | 5.9 | 5.7 | |
| | | | | | | | | 0.2 | 0.5 | 1.1 | 0.6 | 4.5 | 4.3 | |

FIG. 7A (Cont. 2)

| | | | | | | | | | | | | | | |
|---|---|---|---|---|---|---|---|---|---|---|---|---|---|---|
| | 0.03mm | | 15mg | | Coarse | Aged | None | 0.2 | 0.3 | 1.1 | 0.8 | 3.5 | 3.3 | |
| | | | 25mg | 25°C | | | | 0.1 | 0.3 | 4 | 3.7 | 8.5 | 8.4 | |
| | | | | | | | | 0.2 | 0.3 | 5 | 4.7 | 6.7 | 6.5 | |
| | | 2x2cm | 25mg | 25°C | | | | 0.2 | 0.3 | 5.5 | 5.2 | 9.8 | 9.6 | |
| | | | | | | | | 0.2 | 2 | 2 | 0 | 8.2 | 8 | |
| | | | | | | | | 0.2 | 2 | 2 | 0 | 8.2 | 8 | |
| | | | 25mg | 25°C | | | | 0.1 | 0.2 | 3.5 | 3.3 | 9 | 8.9 | Double sealed |
| | | | | | | | | 0.1 | 0.2 | 4.5 | 4.3 | 11.2 | 11.1 | |
| | | | 25mg | 25°C | | | | 0.3 | 1.5 | 5.5 | 4 | 17 | 16.7 | Double bag |
| | | | 50mg | 25°C | | | | 0.2 | 0.3 | 5.5 | 5.2 | 8.2 | 8 | |
| | | | | | | | | 0.2 | 1 | 3 | 2 | 8.2 | 8 | |
| | | | | | | | | 0.2 | 0.3 | 5.5 | 5.2 | 9 | 8.8 | |
| Polyamide 12 | 0.12mm | 2x1cm | 30mg | 37°C | Coarse | Aged | None | 1 | 2 | 6 | 4 | 7.6 | 6.6 | |
| | | | | | | | | 1 | 2 | 4 | 2 | 7.6 | 6.6 | |
| | | | | | | | | 1 | 2 | 4 | 2 | 7.6 | 6.6 | |
| | | | | | | | | 1 | 2 | 4 | 2 | 7.6 | 6.6 | |
| | | | | | | | | 1 | 2 | 4 | 2 | 7.6 | 6.6 | |
| | | | | | | | | 1 | 2 | 6 | 4 | 11 | 10 | |
| | | | | | | | | 1 | 2 | 4 | 2 | 7.6 | 6.6 | |
| | | 2x2cm | 20mg | 25°C | | | | 3 | 3 | 5.5 | 2.5 | 6.5 | 3.5 | (70%-50%) Never full |
| Polyamide Elastomer | 0.06mm | 3.4x1cm | 30mg | 37°C | | | | 0.3 | 0.5 | 0.7 | 0.2 | 1.9 | 1.6 | (95%) Never full |
| | | | | | | | | 0.3 | 0.7 | 0.7 | 0 | 1.9 | 1.6 | |

FIG. 7A (Cont. 3)

| Material | Thickness | Size | Effervescent | Temperature | Grinding | Aging | Desiccant | Rise time | | Last time | | | | Comment |
|---|---|---|---|---|---|---|---|---|---|---|---|---|---|---|
| | | | | | | | | Ta | Tb | Tc | Td | Te | Tf | |
| | | | | | | | | 80% | 100% | | 100% | | 80% | |
| | | | | | | | | 0.3 | 0.7 | 1.5 | 0.8 | 1.9 | 1.6 | |
| Polyether block Amide Copolymer | 0.02mm | 2x1cm | 20mg | 37°C | | | | 0.6 | 2.5 | 2.5 | 0 | 4.8 | 4.2 | |
| | | | | | | | | | | | | | | |
| | | | | | | | | | | | | | | |
| Polyether block Amide Copolymer | 0.08mm | 2x1cm | 20mg | 37°C | | | | 1.2 | 1.5 | 4.5 | 3 | 11.5 | 10.3 | |
| | | | | | | | | 1 | 1.5 | 4.5 | 3 | 11.5 | 10.5 | |
| | | | | | | | | 1 | 1.5 | 4.5 | 3 | 11.5 | 10.5 | |
| | | | | | | | | 0.8 | 1.5 | 4.5 | 3 | 11.5 | 10.7 | |
| | | | | | | | | 1 | 1.5 | 4.5 | 3 | 11.5 | 10.5 | |
| | | | | | | | | 1 | 1.5 | 6 | 4.5 | 24.5 | 23.5 | |
| | | | | | | | | 0.8 | 1.5 | 4.5 | 3 | 11.5 | 10.7 | |
| | | | | | | | | 1 | 1.5 | 6 | 4.5 | 17 | 16 | |
| | | | | | | | | 0.8 | 1.5 | 6 | 4.5 | 17 | 16.2 | |
| | | | | | | | | 1 | 1.5 | 6 | 4.5 | 11.5 | 10.5 | |
| | | 2x2cm | 20mg | 25°C | | | | 4 | 4.5 | 8 | 3.5 | 12.5 | 8.5 | (90%) Never full |
| | | | | | | | | 3.5 | 5.5 | 8 | 2.5 | 12 | 8.5 | |

FIG. 7A (Cont. 4)

| | | | | | | | | | | | | | | |
|---|---|---|---|---|---|---|---|---|---|---|---|---|---|---|
| Polyurethane 55D | 0.05mm | 2x1cm | 15mg | 37°C | Coarse | Aged | None | 0.4 | 0.7 | 0.7 | 0 | 2.6 | 2.2 | |
| | | | | | | | | 0.4 | 0.7 | 0.7 | 0 | 2.4 | 2 | |
| | | | | | | | | 0.4 | 0.5 | 0.7 | 0.2 | 2.4 | 2 | |
| | | | | | | | | 0.4 | 0.7 | 0.7 | 0 | 1.4 | 1 | |
| | | | | | | | | 0.4 | 0.7 | 0.7 | 0 | 2.4 | 2 | |
| | | | 30mg | 37°C | | | | 0.3 | 0.5 | 2.5 | 2 | 4.3 | 4 | |
| | | | | | | | | 0.3 | 0.5 | 2.5 | 2 | 4.6 | 4.3 | |
| | | | | | | | | 0.3 | 0.5 | 2.5 | 2 | 4.6 | 4.3 | |
| | | | | | | | | 0.3 | 0.5 | 2.5 | 2 | 4.6 | 4.3 | |
| | | | | | | | | 0.3 | 0.5 | 2.5 | 2 | 4.6 | 4.3 | |
| Polyurethane 65D | 0.12mm | 2x1cm | 20mg | 37°C | | | | 0.8 | 1.3 | 4.8 | 3.5 | 7.5 | 6.7 | |
| | | | | | | | | 0.8 | 1.3 | 4.8 | 3.5 | 7.5 | 6.7 | |
| | | | | | | | | 0.8 | 1.3 | 4.8 | 3.5 | 7.5 | 6.7 | |
| | | | | | | | | 0.8 | 1.3 | 4.8 | 3.5 | 7.5 | 6.7 | |
| | | | | | | | | 0.8 | 1.3 | 4.8 | 3.5 | 7.5 | 6.7 | |
| Polyurethane | 0.02mm | 2x2cm | 25mg | 37°C | | | | 0.3 | 0.7 | 1 | 0.3 | 1.3 | 1 | (90%) Never full |
| | | | | | | | | 0.5 | 0.7 | 1 | 0.3 | 1.4 | 0.9 | |

FIG. 7A (Cont. 5)

| Material | Thickness | Size | Effervescent | Temperature | Grinding | Aging | Desiccant | Rise time | | Last time | | | | Comment |
|---|---|---|---|---|---|---|---|---|---|---|---|---|---|---|
| | | | | | | | | Ta | Tb | Tc | Td | Te | Tf | |
| | | | | | | | | 80% | 100% | | 100% | | 80% | |
| Thermoplastic Polyurethane Elastomer | 1mils | 30x10mm | 15mg | 37°C | Coarse | Aged | None | 0.6±0.2 | 0.9±0.4 | 1.2±0.5 | 0.3±0.1 | 1.6±0.6 | 1.1±0.4 | |
| | 2mils | 30x10mm | 15mg | 37°C | Coarse | Aged | None | 0.9±0.2 | 1.3±0.1 | 1.6±0.1 | 0.3±0 | 2.4±0.4 | 1.5±0.1 | |
| | 4mils | 30x10mm | 15mg | 37°C | Coarse | Aged | None | 1.4±0.1 | 2.2±0.1 | 2.9±0.2 | 0.7±0.4 | 4.5±0 | 3.2±0.1 | |
| Polyether Block Amide Copolymer | 1mils | 30x10mm | 15mg | 37°C | Coarse | Aged | None | 1.1±0.1 | 1.6±0.1 | 2.4±0.8 | 0.8±0.8 | 2.5±0.1 | 1.4±0.2 | |
| | 2mils | 30x10mm | 15mg | 37°C | Coarse | Aged | None | 1±0.1 | 1.6±0.2 | 2.2±0.4 | 0.7±0.4 | 3.2±0.6 | 2.2±0.5 | |
| | 4mils | 30x10mm | 15mg | 37°C | Coarse | Aged | None | 2±0.3 | 3.4±0.9 | 4.2±0.9 | 0.8±0.3 | 6.3±1.4 | 4.3±1.2 | |
| Thermoplastic Polyurethane Elastomer | 1mils | 30x10mm | 20mg | 37°C | Coarse | Aged | None | 0.9±0.2 | 1.3±0.2 | 1.6±0.1 | 0.4±0.1 | 2.4±0.1 | 1.5±0.1 | |
| | 4mils | 30x10mm | 20mg | 37°C | Coarse | Aged | None | 4.4±0.1 | 6.4±0.3 | 8.2±0.6 | 1.8±0.4 | 11.6±0.6 | 7.2±0.5 | |
| Polyether Block Amide Copolymer | 1mils | 30x10mm | 20mg | 37°C | Coarse | Aged | None | 0.9±0.1 | 1.5±0.1 | 1.9±0.1 | 0.4±0 | 3.1±0.1 | 2.2±0 | |
| | 4mils | 30x10mm | 20mg | 37°C | Coarse | Aged | None | 2.4±0 | 4±0.1 | 5.9±0.1 | 2±0.2 | 8.6±0.2 | 6.2±0.2 | |
| | | 30x10mm | 20mg | 37°C | Coarse | Fresh | None | 1.2±0.1 | 2.3±0.2 | 3.5±0.6 | 1.2±0.6 | 6.6±0.5 | 5.4±0.4 | |
| | | 30x10mm | 20mg | 37°C | Coarse | Fresh | None | 1.3±0.1 | 2.5±0.2 | 4.3±1.2 | 1.8±1.4 | 8.7±1.8 | 7.4±1.8 | |
| | | 30x10mm | 20mg | 37°C | Fine | Fresh | None | 1.1±0.1 | 2.5±0.3 | 4.5±0.4 | 2±0.5 | 10.7±1 | 9.6±0.9 | |
| | | 30x10mm | 20mg | 37°C | Fine | Aged | None | 2±0 | 3.2±0 | 5±0 | 1.8±0 | 8.4±0 | 6.4±0 | |

FIG. 7B

| | | | | | | | | | | | | | | |
|---|---|---|---|---|---|---|---|---|---|---|---|---|---|---|
| Polyether Block Amide Copolymer | 4mils | 30x10mm | 20mg | 37°C | Fine | Fresh | NaCl 20mg | 1.5±0.1 | 2.7±0.2 | 3.9±0.6 | 1.2±0.8 | 9±0.7 | 7.5±0.8 | |
| | | 30x10mm | 20mg | 37°C | Fine | Fresh | PEG 10mg | 1.6±0.2 | 3.6±0.1 | 4.1±0.1 | 0.6±0.1 | 9.4±0 | 7.9±0.2 | |
| | | 30x10mm | 20mg | 37°C | Fine | Fresh | PEG 20mg | 2.2±0.1 | 3.7±0 | 5±0.1 | 1.3±0.1 | 9±0.1 | 6.8±0 | |
| | | 30x10mm | 20mg | 37°C | Fine | Fresh | PEG 30mg | 2.4±0.1 | 3.9±0.1 | 5.5±0.6 | 1.6±0.6 | 10.4±1.2 | 8±1.3 | |
| | | 30x10mm | 20mg | 37°C | Fine | Fresh | CaSO4 20mg | 2.7±0 | 3.9±0 | 4.6±0.1 | 0.7±0.1 | 8.8±0.6 | 6.1±0.6 | |
| | | 30x10mm | 20mg | 37°C | Fine | Fresh | Polyacrylic Acid Sodium Salt 20mg | 18.7±1.9 | 20.9±1.6 | 22.2±1.2 | 1.3±0.4 | 27.1±1.6 | 8.5±0.4 | |
| | | 30x10mm | 20mg | 37°C | Fine | Fresh | CaO2 20mg | 1.3±0.2 | 1.9±0.4 | 2.2±0.5 | 0.3±0.1 | 3.1±1.3 | 1.9±1.1 | |
| | | 30x10mm | 20mg | 37°C | Fine | Fresh | CaCl2 20mg | 7±0 | 9.1±0 | 10.9±0 | 1.8±0 | 11.6±0 | 4.6±0 | |
| Polyamide 6.6 | 0.03mm | 20x10mm | 25mg | 37°C | Fine | Fresh | None | 0.3±0.1 | 0.5±0.2 | 0.7±0.1 | 0.3±0.1 | 2.9±0.1 | 2.7±0.1 | |
| | | 20x10mm | 25mg | 37°C | Fine | 4 Months | None | 0.9±0 | 3±0.8 | 3.3±1.1 | 0.3±0.3 | 5.4±1.2 | 4.5±1.2 | |
| Polyamide 6.6 | 0.03mm | 20x10mm | 5mg | 37°C | Coarse | Aged | None | 0.2±0.1 | 0.9±0.4 | 2.5±0 | 1.6±0.4 | 3.4±0.3 | 3.2±0.4 | |

FIG. 7B (Cont. 1)

| Material | Thickness | Size | Effervescent | Temperature | Grinding | Aging | Desiccant | Rise time | | Last time | | | | Comment |
|---|---|---|---|---|---|---|---|---|---|---|---|---|---|---|
| | | | | | | | | Ta | Tb | Tc | Td | Te | Tf | |
| | | | | | | | | 80% | 100% | | 100% | | 80% | |
| | | 20x10mm | 10mg | 37°C | Coarse | Aged | None | 0.2±0 | 0.4±0.1 | 1.1±0 | 0.7±0.1 | 5.2±1 | 5±1 | |
| | | 20x10mm | 15mg | 37°C | Coarse | Aged | None | 0.2±0 | 0.3±0 | 1.1±0 | 0.8±0 | 3.5±0 | 3.3±0 | |
| | | 20x10mm | 25mg | 25°C | Coarse | Aged | None | 0.2±0.1 | 0.3±0 | 4.5±0.7 | 4.2±0.7 | 7.6±1.3 | 7.5±1.3 | |
| | | 20x20mm | 25mg | 25°C | Coarse | Aged | None | 0.2±0 | 1.4±1 | 3.2±2 | 1.7±3 | 8.7±0.9 | 8.5±0.9 | |
| | | 20x20mm | 25mg | 25°C | Coarse | Aged | None | 0.1±0 | 0.2±0 | 4±0.7 | 3.8±0.7 | 10.1±1.6 | 10±1.6 | Double sealed |
| | | 20x20mm | 25mg | 25°C | Coarse | Aged | None | 0.3±0 | 1.5±0 | 5.5±0 | 4±0 | 17±0 | 16.7±0 | Double bag |
| | | 20x20mm | 50mg | 25°C | Coarse | Aged | None | 0.2±0 | 0.5±0.4 | 4.7±1.4 | 4.1±1.8 | 8.6±0.5 | 8.3±0.5 | |
| Polyamide 12 | 0.12mm | 20x10mm | 30mg | 37°C | Coarse | Aged | None | 1±0 | 2±0 | 4.6±1 | 2.6±1 | 8.1±1.3 | 7.1±1.3 | |
| | | 20x20mm | 20mg | 25°C | Coarse | Aged | None | 3±0 | 3±0 | 5.5±0 | 2.5±0 | 6.5±0 | 3.5±0 | (70%-50%) Never full |
| Polyamide Elastomer | 0.06mm | 34x10mm | 30mg | 37°C | Coarse | Aged | None | 0.3±0 | 0.6±0.1 | 1±0.5 | 0.3±0.4 | 1.9±0 | 1.6±0 | (95%) Never full |
| Polyether Block Amide Copolymer | 0.02mm | 20x10mm | 20mg | 37°C | Coarse | Aged | None | 0.6±0 | 2.5±0 | 2.5±0 | 0±0 | 4.8±0 | 4.2±0 | |
| Polyether Block Amide Copolymer | 0.08mm | 20x10mm | 20mg | 37°C | Coarse | Aged | None | 1±0.1 | 1.5±0 | 5.1±0.8 | 3.6±0.8 | 13.9±4.4 | 12.9±4.4 | |
| | | 20x20mm | 20mg | 25°C | Coarse | Aged | None | 3.8±0.4 | 5±0.7 | 8±0 | 3±0.7 | 12.3±0.4 | 8.5±0 | (90%) Never full |
| Polyurethane 55D | 0.05mm | 20x10mm | 15mg | 37°C | Coarse | Aged | None | 0.4±0 | 0.7±0.1 | 0.7±0 | 0±0.1 | 2.2±0.5 | 1.8±0.5 | |
| | | 20x10mm | 30mg | 37°C | Coarse | Aged | None | 0.3±0 | 0.5±0 | 2.5±0 | 2±0 | 4.5±0.1 | 4.2±0.1 | |
| Polyurethane 65D | 0.12mm | 20x10mm | 20mg | 37°C | Coarse | Aged | None | 0.8±0 | 1.3±0 | 4.8±0 | 3.5±0 | 7.5±0 | 6.7±0 | |
| | | | | | Coarse | Aged | None | | | | | | | |
| Polyurethane | 0.02mm | 20x20mm | 25mg | 37°C | Coarse | Aged | None | 0.4±0.1 | 0.7±0 | 1±0 | 0.3±0 | 1.4±0.1 | 1±0.1 | (90%) Never full |

FIG. 7B (Cont. 2)

| | Effervescent | Start Weight (mg) | After 12hr Weight (mg) | Percent Weight Increase | Weight Increase (mg) |
|---|---|---|---|---|---|
| Polyamide 6.6 | 10mg | 42 | 121 | 188.10% | 79 |
| | | 47 | 124 | 163.83% | 77 |
| | 20mg | 56 | 161 | 187.50% | 105 |
| | | 52 | 159 | 205.77% | 107 |
| | 30mg | 66 | n/a | n/a | n/a |
| | | 66 | 174 | 163.64% | 108 |
| Polyether Block Amide Copolymer 4mils | 15mg | 99 | 103 | 4.04% | 4 |
| | | 103 | 106 | 2.91% | 3 |
| | 20mg | 104 | 109 | 4.81% | 5 |
| | | 101 | 106 | 4.95% | 5 |
| | 30mg | 115 | 120 | 4.35% | 5 |
| | | 117 | 120 | 2.56% | 3 |
| | 20mg (aged) | 103 | 110 | 6.80% | 7 |
| | | 98 | 107 | 9.18% | 9 |
| | 20mg + 10mg PEG | 112 | 120 | 7.14% | 8 |
| | | 111 | 117 | 5.41% | 6 |
| | 20mg + 20mg PEG | 127 | 132 | 3.94% | 5 |
| | | 122 | 128 | 4.92% | 6 |
| | 20mg + 30mg PEG | 138 | 142 | 2.90% | 4 |
| | | 135 | 141 | 4.44% | 6 |
| Polyamide 12 | 20mg | 125 | 133 | 6.40% | 8 |
| | | 128 | 134 | 4.69% | 6 |
| | 30mg | 136 | 143 | 5.15% | 7 |
| | | 143 | 150 | 4.90% | 7 |
| Polyurethane 55D | 20mg | 87 | 101 | 16.09% | 14 |
| | | 90 | 104 | 15.56% | 14 |
| | 30mg | 94 | 110 | 17.02% | 16 |
| | | 96 | 112 | 16.67% | 16 |
| Polyurethane 65D | 20mg | 170 | 180 | 5.88% | 10 |
| | | 168 | 179 | 6.55% | 11 |
| | 30mg | 178 | 188 | 5.62% | 10 |
| | | 182 | 193 | 6.04% | 11 |
| Thermoplastic Polyurethane Elastomer 1mils | 15mg | 46 | 62 | 34.78% | 16 |
| | | 43 | 57 | 32.56% | 14 |
| | 20mg | 50 | 70 | 40.00% | 20 |
| | | 52 | 72 | 38.46% | 20 |
| | 30mg | 64 | 100 | 56.25% | 36 |
| | | 62 | 98 | 58.06% | 36 |
| Thermoplastic Polyurethane Elastomer 2mils | 15mg | 70 | 85 | 21.43% | 15 |
| | | 73 | 88 | 20.55% | 15 |
| | 20mg | 78 | 94 | 20.51% | 16 |
| | | 79 | 95 | 20.25% | 16 |
| | 30mg | 86 | 108 | 25.58% | 22 |

FIG. 7C

| | Effervescent | Start Weight (mg) | After 12hr Weight (mg) | Percent Weight Increase | Weight Increase (mg) |
|---|---|---|---|---|---|
| | | 82 | 102 | 24.39% | 20 |
| Thermoplastic Polyurethane Elastomer 4mils | 15mg | 137 | 147 | 7.30% | 10 |
| | | 147 | 158 | 7.48% | 11 |
| | 20mg | 150 | 161 | 7.33% | 11 |
| | | 148 | 159 | 7.43% | 11 |
| | 30mg | 153 | 165 | 7.84% | 12 |
| | | 157 | 167 | 6.37% | 10 |
| Polyether Block Amide Copolymer 1mils | 15mg | 36 | 51 | 41.67% | 15 |
| | | 30 | 39 | 30.00% | 9 |
| | 20mg | 40 | 59 | 47.50% | 19 |
| | | 40 | 57 | 42.50% | 17 |
| | 30mg | 51 | 64 | 25.49% | 13 |
| | | 50 | 62 | 24.00% | 12 |
| Polyether Block Amide Copolymer 2mils | 15mg | 56 | 65 | 16.07% | 9 |
| | | 54 | 60 | 11.11% | 6 |
| | 20mg | 66 | 77 | 16.67% | 11 |
| | | 66 | 78 | 18.18% | 12 |
| | 30mg | 73 | 79 | 8.22% | 6 |
| | | 76 | 82 | 7.89% | 6 |

All effervescent are fresh; unless specified

FIG. 7C (Cont.)

CAPSULE DEVICE HAVING VARIABLE SPECIFIC GRAVITY

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS REFERENCE TO RELATED APPLICATIONS

The present invention is related to PCT Patent Application Series No. PCT/US13/66011 entitled "System and Method for Capsule Device with Multiple Phases of Density", filed on Oct. 22, 2013, PCT Patent Application Series No. PCT/US13/39317, entitled "Optical Wireless Docking System for Capsule Camera", filed on May 2, 2013 and PCT Patent Application Series No. PCT/US13/42490, entitled "Capsule Endoscopic Docking System", filed on May 23, 2013. The U.S. Patent and PCT Patent Applications are hereby incorporated by reference in their entireties.

BACKGROUND OF THE INVENTION

Field of the Invention

The present invention relates to diagnostic imaging inside the human body. In particular, the present invention relates to a capsule device with a variable specific gravity for diagnostic imaging of the Gastrointestinal (GI) tract.

Description of the State of the Art

Devices for imaging body cavities or passages in vivo are known in the art and include endoscopes and autonomous encapsulated cameras. Endoscopes are flexible or rigid tubes that pass into the body through an orifice or surgical opening, typically into the esophagus via the mouth or into the colon via the rectum. An image is formed at the distal end using a lens and transmitted to the proximal end, outside the body, either by a lens-relay system or by a coherent fiber-optic bundle. A conceptually similar instrument might record an image electronically at the distal end, for example using a CCD or CMOS array, and transfer the image data as an electrical signal to the proximal end through a cable. Endoscopes allow a physician control over the field of view and are well-accepted diagnostic tools. However, they do have a number of limitations, present risks to the patient, are invasive and uncomfortable for the patient. Additionally, patient costs typically associated with imaging body cavities with an endoscope prohibits their use as a routine health-screening tool.

Because of the difficulty traversing a convoluted passage, endoscopes cannot easily reach the majority of the small intestine. Special techniques and precautions are needed to reach the entirety of the colon. Endoscopic risks include the possible perforation of bodily organs traversed and complications arising from anesthesia. A trade-off is often made between the extent of imaging taken of body cavities and patient pain during the procedure, health risks and/or post-procedural down time associated with the use of anesthesia. Also, a large number of patients are uncomfortable with the concept of traditional endoscopy and are therefore refusing the procedure resulting in an increased risk of colorectal cancer.

An alternative in vivo image sensor that addresses many of these problems is the capsule endoscope. A camera is housed in a swallowable capsule, along with a radio transmitter for transmitting data, primarily comprising images recorded by the digital camera, to a base-station receiver or transceiver and data recorder outside the body. The capsule may also include a radio receiver for receiving instructions or other data from a base-station transmitter. Instead of radio-frequency transmission, lower-frequency electromagnetic signals may be used. Power may be supplied inductively from an external inductor to an internal inductor within the capsule or from a battery within the capsule.

An autonomous capsule camera system with on-board data storage was disclosed in the U.S. Pat. No. 7,983,458, entitled "In Vivo Autonomous Camera with On-Board Data Storage or Digital Wireless Transmission in Regulatory Approved Band," granted on Jul. 19, 2011. This patent describes a capsule system using on-board storage such as semiconductor nonvolatile archival memory to store captured images. After the capsule passes from the body, it is retrieved. A capsule housing is opened and the images stored are transferred to a computer workstation for storage and analysis. For capsule images either received through wireless transmission or retrieved from on-board storage, the images are displayed and examined by a diagnostician to identify potential anomalies. Alternatively, the nonvolatile archival memory may be located separately or remotely from the capsule and the images transmitted to this memory over a wireless data link.

FIG. 1 illustrates an exemplary capsule sensing system with on-board storage. The sensing system 110 includes illuminating system 12 and a camera that includes optical system 14 and image sensor 16. A semiconductor nonvolatile archival memory 20 may be provided to allow the images to be stored and later retrieved at a docking station outside the body, after the capsule is recovered. The sensing system 110 includes battery power supply 24 and an output port 26.

Sensing system 110 may be propelled through the GI tract by peristalsis. Illuminating system 12 may be implemented by LEDs. In FIG. 1, the LEDs are located adjacent to the camera's aperture, although other configurations are possible. A light source may also be provided, for example, behind the aperture. Other light sources, such as laser diodes, may also be used. Alternatively, white light sources or a combination of two or more narrow-wavelength-band sources may also be used. White LEDs are available that may include a blue LED or a violet LED, along with phosphorescent materials that are excited by the LED light to emit light at longer wavelengths. The portion of capsule housing 10 that allows light to pass through may be made from bio-compatible glass or polymer.

Optical system 14, which may include multiple refractive, diffractive, or reflective lens elements, provides an image of the lumen walls on image sensor 16. Image sensor 16 may be provided by charged-coupled devices (CCD) or complementary metal-oxide-semiconductor (CMOS) type devices that convert the received light intensities into corresponding electrical signals. Image sensor 16 may have a monochromatic response or include a color filter array such that a color image may be captured (e.g. using the RGB or CYM representations). The analog signals from image sensor 16 are preferably converted into digital form to allow processing in digital form. Such conversion may be accomplished using an analog-to-digital (A/D) converter, which may be provided inside the sensor (as in the current case), or in another portion inside capsule housing 10. The A/D unit may be provided between image sensor 16 and the rest of the system. LEDs in illuminating system 12 are synchronized with the operations of image sensor 16. Processing module 22 may be used to provide processing required for the system such as image processing and video compression. The processing module may also provide needed system control such as to control the LEDs during image capture operation. The processing module may also be responsible for other functions, such as managing image capture and coordinating image retrieval.

After traveling through the GI tract and exiting from the body, the capsule camera is retrieved. Its images stored in an archival memory are read out through an output port. The received images are usually transferred to a base station for processing and for a diagnostician to examine. The accuracy as well as efficiency of diagnostics is most important. A diagnostician is expected to examine all images and correctly identify all anomalies.

As the capsule device travels through the gastrointestinal (GI) tract, the capsule device will encounter different environments. It is desirable to manage the capsule device to travel at a relatively steady speed so that sufficient sensor data (e.g., images) is collected along the desired portion of the GI tract and without wasting power or excessive data collection.

Naturally, the density of the capsule can affect its motion through a body liquid. If the capsule density is greater than the body liquid in which it is found, the capsule will tend to move in the direction of gravity. If the capsule density is less than the body liquid density and in the absence of peristalsis, the capsule will tend to move against gravity or remain at its location, since the volume of fluid displaced by the capsule weighs more than the capsule. Thus, for a capsule intended for collecting images in the colon including the ascending colon it is desirable to have a density ratio (i.e., (capsule density)/(body liquid)) or Specific Gravity (SG)<1, but also have SG>1 before the capsule reaches the large intestine, such as when the capsule is passing through the stomach.

SUMMARY OF THE INVENTION

The present invention discloses a capsule device capable of having its density change or vary as it travels through the gastrointestinal (GI) tract. The capsule device comprises a sensor system and a density control. The sensor system may include a light source, an image sensor for capturing image frames of a scene illuminated by the light source, an archival memory, and housing. The light source and image sensor are enclosed within the housing. The archival memory may be enclosed within the housing, or separate from the housing. In the latter case the archival memory may be accessed remotely by a wireless link with the capsule device. The capsule device is intended for being swallowed by a patient.

Embodiments of the capsule device's density control include a pouch containing an effervescent mixture. In some embodiments there is one pouch containing an effervescent. In other embodiments there can be more than one pouch, each containing an effervescent. The pouch is made at least partially from a fluid-permeable membrane material. Body fluid diffuses through the membrane to mobilize and initiate the effervescent reaction, which tests show has the effect of reducing the SG of the capsule device from between well above and slightly below 1, for the purpose of facilitating passage of the capsule through different regions of the GI tract. In some embodiments the capsule SG can vary between about 1.1 and 2.0 (SG>1) and equal to and less than 1, such as between 1.0 and about 0.84, or between about 0.98 and 0.87 (SG≤1). Preferably a pouch or deformable member, or at least a portion thereof, is made from a material or materials that prevent or minimize diffusion of the effervescent gas. Preferably, the at least a portion of the pouch or deformable member is made from a material or materials that are permeable but minimally permeable to CO2 gas and water.

In respect to transit through the GI tract, there are at least two designated regions where the capsule SG can differ. In one embodiment, the capsule SG is greater than one for the stomach and less than one for the ascending colon. In another embodiment the capsule SG is less than one for the ascending colon and greater than one for the stomach and descending colon in order to have the capsule device assume a desired specific gravity within the GI tract, it is helpful to have a good understanding of transit times through regions of the GI tract. These transit times will of course vary from person to person and depend on such factors as the age, gender, race, health and anatomy of the patient. In some embodiments the capsule SG may be configured to change, i.e., increase or decrease, based on an elapsed time from when the patient swallows the capsule to when the capsule should have reached the region of interest, e.g., time from swallowing the capsule to when it has passed through the pyloric valve.

Other embodiments of a capsule device with deformable member (e.g., a tethered pouch containing an effervescent mixture) include a deformable member coated with a biodegradable, bio-erodible or bioresorbable coating to prevent body liquid from diffusing into an interior of the deformable member for a limited period of time, e.g., prior to the capsule device passing through the stomach. Other embodiments include a capsule device encased or encapsulated within a biodegradable shell that encloses the entire capsule device, or a dome that only partially encloses the capsule device. The coating, dome or shell embodiments prevent body liquid from coming into contact with the deformable member until the coating, dome or shell has fully or partially degraded within the body liquid. The coating, shell or dome is configured to degrade after the capsule device has passed through a portion of the GI tract. As such, a capsule device with a SG>1 is maintained until after essentially all of the biodegradable coating, shell or dome has degraded or resorbed and a fluid-permeable membrane material comes into contact with body liquid. The coating material, or material or the shell or dome, may be essentially water soluble, enzymatic or enteric material.

A sensing system of the capsule device may have electrical contacts fixedly disposed on the housing, wherein the electrical contacts are coupled to the archival memory so that an external device is allowed to access image data stored in the archival memory through the electrical contacts. The electrical contacts may include power pins to provide power to the capsule device for data retrieval of image data stored on the archival memory. Alternatively, inductive powering can be used to provide power to the capsule device for data retrieval of image data stored on the archival memory. In yet another embodiment, the capsule device further comprises an optical transmitter to transmit an optical signal through a clear window, wherein image data from the archival memory is transmitted to an external optical receiver.

According to one aspect of the invention, there is a capsule device, a capsule endoscope, a method for making such a capsule device/endoscope, a method for assembly of a capsule device/endoscope, a system or a method for imaging of the GI Tract including but not limited to the colon using the capsule device having one or more, or any combination of the following items (1) through (8):

(1) Enteric coating, dome or shell; time-controlled coating, dome or shell; water-soluble coating, dome or shell; and/or enzymatic coating, dome or shell.

(2) The Embodiment A including one or more or, or any combination of the parameters (a) through (i) associated with Embodiment A.

(3) The Embodiment B including one or more or, or any combination of the parameters (a) through (i) associated with Embodiment B.

(4) Any of the embodiments of a pouch disclosed in FIG. 7A (5) Non-volatile, archival memory for storing images, located on device or accessed remotely by the system.

(6) A capsule endoscope, comprising: a sensor system comprising a light source, an image sensor for capturing image frames of a scene illuminated by the light source, and an archival memory; a housing adapted for being swallowed, wherein the sensor system is enclosed in the housing; and a pouch containing an effervescent, the pouch being attached to the housing; wherein at least the pouch is encapsulated within a dissolvable shell, dome or coating; and wherein the endoscope specific gravity (SG) is greater than 1 when the pouch is not submerged in water.

(7) Item (6) in combination with one or more, or any combination of the following items (6.a) through (6.$) with item (6): (6.a) wherein at least the pouch is encapsulated within an enteric shell, dome or coating; (6.b) wherein the enteric coating, dome or coating is designed to a pH in the range of 5.0-7.4 so that the coating, dome or shell is intended to dissolve in the small intestine; (6.c) wherein the endoscope is configured such that the specific gravity (SG) drops below 1 in about two hours after the pouch is exposed to water; (6.d) wherein the endoscope is configured such that the specific gravity (SG) is less than 1 for more than about six hours after the pouch is exposed to water; (6.e) wherein the pouch comprises polyetherblockamide copolymers, thermoplastic polyurethanes, polyamides, polyamide block copolymers, polyamide elastomers, polyurethanes, polyesters, polyester copolymers, polyamide copolymers, polyurethane copolymers, polyether copolymers, polyesteramides, polyesteramide copolymers, polyvinyl chloride, polyvinyl chloride copolymers, polyvinylidene dichloride, polyvinylidene dichloride copolymers, fluoropolymers, polyvinyl fluoride, polyvinyl fluoride copolymers, polyvinylidene difluoride, polyvinylidene difluoride copolymers, polyvinylpyrrolidone copolymers, or polyvinylalcohol copolymers; (6.f) wherein the pouch has a wall thickness of less than 5 mils or less than 10 mils; (6.g) wherein the pouch water uptake in 12 hours relative to a pouch and effervescent dry weight is less than 200% or 50%; (6.h) wherein the pouch material is selected form the set consisting of polyetherblockamide copolymers, thermoplastic polyurethanes, polyamides, polyamide block copolymers, polyamide elastomers, polyurethanes, polyesters, polyester copolymers, polyamide copolymers, polyurethane copolymers, polyether copolymers, polyvinyl chloride, polyvinyl chloride copolymers, polyvinylidene dichloride, polyvinylidene dichloride copolymers, fluoropolymers, polyvinyl fluoride, polyvinyl fluoride copolymers, polyvinylidene difluoride, or polyvinylidene difluoride copolymers; (6.i) wherein the Young's modulus of the pouch is: high enough to create a non-conformal pouch; or low enough to create a slightly conformal pouch, such that the pouch can reach a maximum size 25% above the nominal size with a maximum of 40 mg effervescent; (6.j) wherein the endoscope pouch is configured such that the specific gravity (SG) is more than for more than 1.5 hours after the pouch is exposed to water; (6.k) wherein the endoscope pouch is configured such that the specific gravity (SG) is <1 for more than 6 hours after the pouch is exposed to water; (6.l) wherein the endoscope pouch is configured such that the specific gravity (SG) is <1 for more than 4 hours after the pouch is exposed to water; (6.m) wherein the endoscope pouch is configured such that the specific gravity (SG) is <1 for more than 4 hours but less than 12 hours; (6.n) wherein the effervescent is coated; (6.o) wherein the effervescent coating is an enteric coating designed to a pH in the range of 5.0-7.4 such that the effervescent is intended to react with water after the endoscope has reached the small intestine; (6.p) wherein the pouch further comprises a desiccant; (6.q) wherein the ratio of desiccant to effervescent is 1:10 to 2:1; (6.r) wherein the pouch has a total exterior surface area of about 300 and 1,000 mm2 and where the active exterior surface area is between about 50 and 1,000 mm2; and/or (6.s) wherein between about 10 mg and 50 mg of effervescent are contained within the pouch.

(8) One, two, three or more pouches attached to the capsule.

INCORPORATION BY REFERENCE

All publications and patent applications mentioned in the present specification are herein incorporated by reference to the same extent as if each individual publication or patent application was specifically and individually indicated to be incorporated by reference. To the extent there are any inconsistent usages of words and/or phrases between an incorporated publication or patent and the present specification, these words and/or phrases will have a meaning that is consistent with the manner in which they are used in the present specification.

BRIEF DESCRIPTION OF THE DRAWINGS

FIGS. 2A and 2B show the capsule device before and after placing the device in a dissolvable shell, such as an enteric or non-enteric shell. FIG. 2C illustrates the device after the shell has dissolved and the pouch is exposed to water. FIG. 2D illustrates the state of the device after the pouch has accumulated water and the CO2 has substantially diffused out of the pouch.

FIG. 7A summarizes results from bench tests of inflation periods for several different pouch configurations according to the disclosure.

FIG. 7B report statistics (mean and standard deviation) for some of the bench tests in FIG. 7A.

FIG. 7C is a table showing the percent and amount of weight increase for different pouch configurations. The change in weight is measured after the pouch was submerged for 12 hours. The weight percentage change is measured with respect to the dry weight of the pouch with effervescent and desiccant inside. For three of the cases PEG was added as a desiccant, polyacrylic acid sodium salt homo- and co-polymers are also effective polymer desiccants.

DETAILED DESCRIPTION

Figure 1:
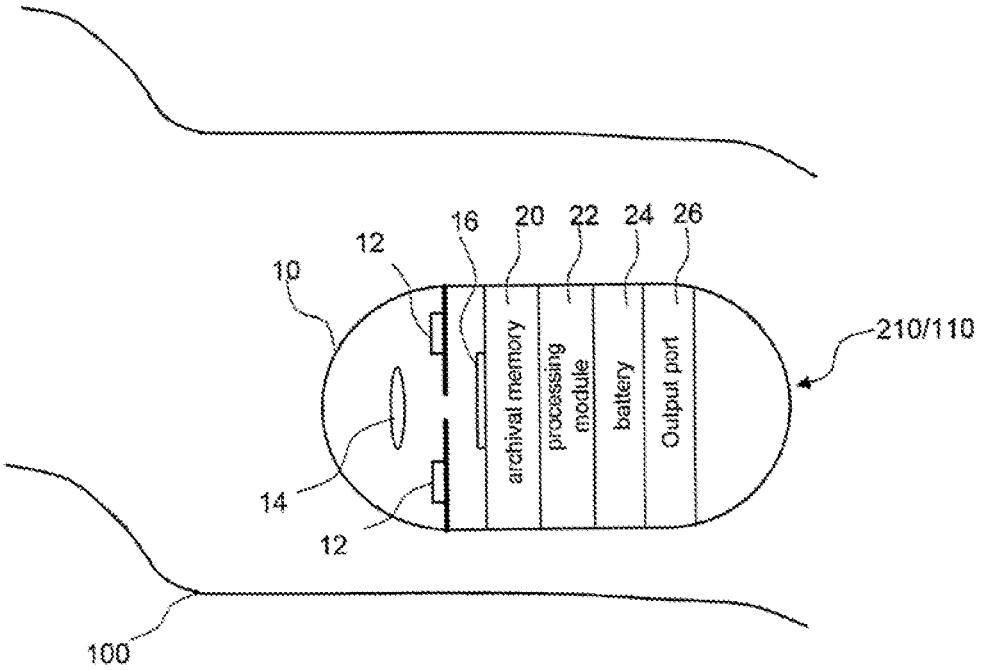
FIG. 1 shows schematically a capsule camera system in the GI tract, where archival memory is used to store captured images to be analyzed and/or examined.

It will be readily understood that the components of the present invention, as generally described and illustrated in the figures herein, may be arranged and designed in a wide variety of different configurations. Thus, the following more detailed description of the embodiments of the systems and methods of the present invention, as represented in the figures, is not intended to limit the scope of the invention, as claimed, but is merely representative of selected embodiments of the invention.

Reference throughout this specification to "one embodiment," "an embodiment," or similar language means that a particular feature, structure, or characteristic described in connection with the embodiment may be included in at least one embodiment of the present invention. Thus, appearances of the phrases "in one embodiment" or "in an embodiment" in various places throughout this specification are not necessarily all referring to the same embodiment.

Furthermore, the described features, structures, or characteristics may be combined in any suitable manner in one or more embodiments. One skilled in the relevant art will recognize, however, that the invention can be practiced without one or more of the specific details, or with other methods, components, etc. In other instances, well-known structures, or operations are not shown or described in detail to avoid obscuring aspects of the invention.

The illustrated embodiments of the invention will be best understood by reference to the drawings, wherein like parts are designated by like numerals throughout. The following description is intended only by way of example, and simply illustrates certain selected embodiments of apparatus and methods that are consistent with the invention as claimed herein.

In the description like reference numbers appearing in the drawings and description designate corresponding or like elements among the different views.

For purposes of this disclosure, the following terms and definitions apply:

The terms "about" or "approximately" mean 30%, 20%, 15%, 10%, 5%, 4%, 3%, 2%, 1.5%, 1%, between 1-2%, 1-3%, 1-5%, or 0.5%-5% less or more than, less than, or more than a stated value, a range or each endpoint of a stated range, or a one-sigma, two-sigma, three-sigma variation from a stated mean or expected value (Gaussian distribution). For example, d1 about d2 means d1 is 30%, 20%, 15%, 10%, 5%, 4%, 3%, 2%, 1.5%, 1%, 0% or between 1-2%, 1-3%, 1-5%, or 0.5%-5% different from d2. If d1 is a mean value, then d2 is about d1 means d2 is within a one-sigma, two-sigma, or three-sigma variance from d1.

It is understood that any numerical value, range, or either range endpoint (including, e.g., "approximately none", "about none", "about all", etc.) preceded by the word "about," "substantially" or "approximately" in this disclosure also describes or discloses the same numerical value, range, or either range endpoint not preceded by the word "about," "substantially" or "approximately."

An "enteric" coating, or coated shell or dome, or a dome or shell made from an enteric material dissolves when immersed in a pH environment of greater than about 5, or that dissolves in the small intestine but not in the stomach.

A shell or dome not coated with an enteric coating, or a "non-enteric" coating, or a shell or dome not made from an enteric material dissolves when immersed in bodily fluids at physiological temperatures. A water soluble coating or material made from gelatin or hydroxyl propyl methyl cellulose (HPMC) are examples.

A "water soluble" or "time-released" coating, shell or dome is a water soluble coating, dome or shell that dissolves in gastric juices or water. The coating, shell or dome can be made to dissolve from between about 3, 5, or 10 minutes to 4 hours from the time when it is put in contact with body fluid.

An "enzymatic" coating, shell or dome is a coating, shell or dome constructed to dissolve when it comes in contact with enzymes in the body.

A "time controlled" coating, shell or dome is a coating, shell or dome constructed to dissolve within a predetermined amount of time. A time-controlled coating may be water soluble.

"Body liquid" means a gastric liquid, liquid present in the GI tract when the capsule device is in transit, water or a liquid in the GI tract that is substantially water.

"Specific Gravity" or SG means the ratio of the density of a body to the density of water at 37 Deg. Celsius. A body that is buoyant or floats on the surface of water has its SG equal to about one or less than one. A body that sinks in water has an SG greater than one.

"a deformable member" means a body including a pouch, balloon, sack, or bag made at least partially from a fluid-permeable membrane material. In a preferred embodiment at least a portion of the deformable member is made from a fluid-permeable membrane material that is permeable but minimally permeable to water and CO2 gas.

In preferred embodiments the deformable member includes a pouch made entirely from a fluid-permeable membrane material that prevents or minimizes diffusion of the effervescent gas, a tether for attaching the pouch to a capsule housing, and an effervescent contained within the pouch. The pouch is sealed so that a fluid can enter its interior only by diffusion through the membrane. In some embodiments there can be more than one pouch.

A "desiccant" is a solid that absorbs water and does not release a gas when it encounters water. A desiccant may be silica gel, sodium chloride, CaCl2, MgSO4, Na2SO4, CaSO4, K2CO3, Na2CO3, NaHCO3, CaO, BaO, Al2O3, P2O5, polymers and super absorbing polymers such as polyethylene glycol (PEG), polyvinylalcohol (PVA), polyvinylpyrrolidone (PVP), cellulose, alginate, polyacrylonitrile starch graft copolymers, acylic acid acrylamide copolymers, polyvinyl alcohol copolymers, polyacrylate polyacrylamide copolymers, sodium polyacylate or polyacrylic acid sodium salt (works with potassium as well), polyacryl amide copolymer, ethylene malic anhydride copolymer, crosslinked carboxymethylclulose, and crosslinked polyethylene oxide. The polymers can be of any molecular weight from about 3,000 to 500,000 Daltons, or have any structure such as linear, branched, star, dendritic, or a combination of these structures.

An "effervescent" or "gas generating material" is a biocompatible material that when placed in aqueous solution generates carbon dioxide (CO2) or another gas. A mixture of anhydrous sodium bicarbonate and anhydrous citric acid is one example of an effervescent, a mixture of potassium bicarbonate and anhydrous citric acid is another example, a mixture of two or more bicarbonate salts and anhydrous citric acid is another example. In another embodiment citric acid is replaced by another anhydrous solid state acid such as ascorbic acid or succinic acid. In preferred embodiments an effervescent mixture is used.

U.S. Pat. No. 7,192,397 and U.S. Pat. No. 8,444,554 disclose a capsule device. If the capsule SG is about 1 the device will suspend or float in the liquid in the gastrointestinal (GI) tract such as in the stomach or in the colon. As disclosed in U.S. Pat. No. 7,192,397 and U.S. Pat. No. 8,444,554, the capsule device will be carried through the small and large intestine by backpressure of a flow of liquid through the body lumen when the capsule SG is about 1. However, a capsule SG of about 1 or less than 1 may float in the stomach for some time, rather than passing through the pyloric valve. Thus, on the one hand, it is desirable to have the capsule SG>1 so that the capsule device will pass through the stomach without much difficulty. On the other hand, a capsule device with SG>1 will not will easily ascend the colon, or may sit stationary in the cecum for a long period of time. Capsule devices according to one aspect of the disclosure can, however, traverse the ascending colon by having the capsule device SG become less than 1 by the time the capsule device reaches the cecum.

For a capsule device with an image sensor, it is desirable to have a steady and consistent travelling velocity inside different regions of the GI tract, e.g. stomach, small bowel, ascending and descending colons so that smooth and stable images and video can be obtained. The travelling velocity of the capsule camera depends on many factors including regional gastrointestinal motility, gravitational force, buoyancy and viscous drag of the surrounding fluids. After the capsule device is swallowed, it is propelled into the esophagus. Peristaltic waves in the esophagus move the capsule device into the stomach. After the capsule device passes the cardia and enters the stomach fluid, the balance among gravitational force, buoyancy and drag from the gastric fluids starts to affect its travelling velocity and transit time. Travel through the stomach for the capsule device may be understood through the migrating myoelectric complex or cycle (MMC). The MMC can be divided into four phases. Phase 1 lasts between 30 and 60 minutes with rare contractions. Phase 2 lasts between 20 and 40 minutes with intermittent contraction. Phase 3, or housekeeping phase, lasts between 10 and 20 minutes with intense and regular contractions for short period. The housekeeping wave sweeps all the undigested material out of the stomach to the small bowel. Phase 4 lasts between 0 and 5 minutes and occurs between phase 3 and phase 1 of two consecutive cycles. In the small intestine, the BER (basic electrical rhythm) is around 12 cycles/minute in the proximal jejunum and decreases to 8 cycles/minutes in the distal ileum. There are three types of smooth muscle contractions: peristaltic waves, segmentation contractions and tonic contractions. Normally, peristalsis will propel the capsule device towards the large intestines.

While the large intestine is one organ, it demonstrates regional differences. The right or proximal (ascending) colon serves as a reservoir and the distal (transverse and descending) colon mainly performs as a conduit. The character of the luminal contents impacts the transit time. Liquid passes through the ascending colon quickly, but remains within the transverse colon for a long period of time. In contrast, a solid meal is retained by the cecum and ascending colon for longer periods than a liquid diet. In the ascending colon, retrograde movements are normal and occur frequently. In order for the buoyant force to overcome the gravitational force and retropulsion, the specific gravity of the capsule device may be decreased to less than one (e.g., about 0.94 or less) by the time the capsule device enters the large intestine. Additionally, the capsule device may have its SG increased back to above 1 by the time it reaches the transverse or descending colon to shorten the transit time to the rectum, and/or to facilitate or more smooth and steady motion to the rectum.

In order to properly set the specific gravity of a capsule device, one of course needs to know when the capsule device will arrive (or has arrived) at specific regions of the GI tract. There are various known region detection methods in the literature. The region detection methods include estimated transit time (e.g., about 1 hour in stomach and about 3-4 hours in small bowel), identification of image contents based on captured images by the capsule device, motion detection based on the captured images by the capsule device, pH detection (pH value increasing progressively from the stomach (1.5-3.5) and the small bowel (5.5-6.8) to the colon (6.4-7.0), pressure sensor (higher luminal pressure from peristaltic motion in the colon than that in the small bowel) and colonic microflora. The ascending colon has a larger diameter than other regions besides the stomach. The size may be detected by the methods disclosed in U.S. Patent Publications, Series No. 2007/0255098, published on Nov. 1, 2007, U.S. Patent Publications, Series No. 2008/0033247 published on Feb. 7, 2008 and U.S. Patent Publications, Series No. 2007/0249900, published on Oct. 25, 2007.

According to some embodiments, the capsule device is configured to have a specific gravity (SG) larger than 1 when the device resides in the stomach. For example, the capsule device SG is about 1.1, or between 1.1 and 2. After the capsule device passes through the small bowel and enters the cecum, it must traverse the ascending colon. The capsule device SG is reduced to less than 1 (e.g., about 0.94) by the time it reaches the ascending colon. By reducing the SG the procedure time should not unnecessarily be prolonged so that patient does not need to fast for too long. Furthermore, the battery life for the capsule device is limited. If the capsule device stays in the ascending colon for too long, the battery may be exhausted before the capsule device finishes its intended tasks, such as capturing images of the colon. Therefore, it is preferred that the capsule device has a specific gravity less than 1 by the time it reaches the cecum or ascending colon. For example, the capsule device may have an SG of about 0.94 or less. During the intermediary period between the stomach and large intestine the capsule device may have a SG of less than or greater than 1. In some embodiments, the capsule device may evolve into a first state with a specific gravity greater than 1 when the capsule device resides in the stomach; the capsule device then evolves into a second state with a specific gravity less than 1 by the time the capsule device reaches the ascending colon; and the capsule device further evolves into a third state with a specific gravity greater than 1 or with a density heavier than the liquid by the time it reaches the descending colon. Finally the capsule device will reach the anus for excretion. An SG of about 1.1 or larger may be selected for the stomach and descending colon and a specific gravity of 0.94 or smaller may be selected for the ascending colon. The embodiments of a deformable member where the SG slower changes based on the rates of diffusion of gas or liquid is an example of an evolving SG capsule device.

FIGS. 2A through 2D depict a capsule device 120 including a deformable member 140 tethered to the housing 10 of the sensing system 110 (FIG. 1).

Figure 2A:
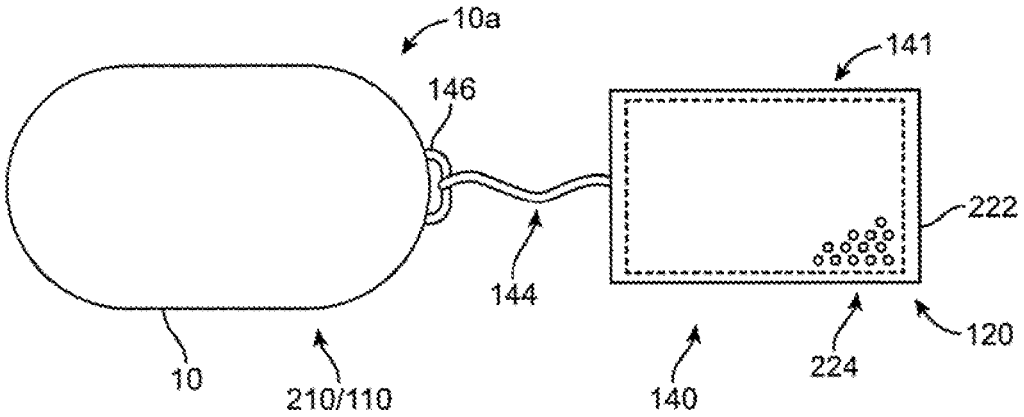
FIGS. 2A through 2D illustrate a capsule device having an attached pouch.

FIG. 2A depicts an assembled view showing the capsule device 120 prior to being encased or encapsulated within a shell 130 configured to transport the device 120 to a target region of the GI tract, e.g., the stomach or the duodenum. The deformable member 140 includes a pouch 141 formed from a semi-permeable or porous membrane 222, an effervescent 224 contained within an interior of the pouch 141 and a tether 144 connecting the pouch 140 to the housing 10. The tether 144 is secured to a loop 146 disposed at an end 10a of the housing 10.

FIG. 2A depicts the capsule device before the deformable member 140 expands in response to the effervescent 224 being exposed to body liquid. The pouch 140 interior space is sealed from its exterior environment, thereby allowing a fluid to pass in/out of the pouch interior only through diffusion through its membrane 222 (an assembly of the deformable member 140 is discussed in connection with FIGS. 4A through 4E).

Figure 2B:
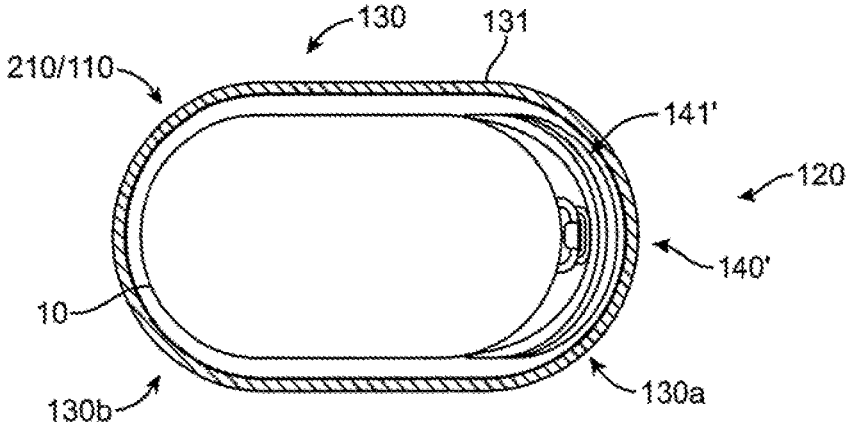

FIG. 2B shows the capsule device 120 within a biodegradable shell 130, which may be water soluble or enteric. The shell 130 has a front piece or portion 130a shaped to form a space for the deformable member 140'. The folded pouch 141' is packed within this open space provided at the front piece/portion 130a of the shell 130. The shell 130 may be made in two pieces (i.e., a front piece 130a and rear piece 130b) that are secured together and may be coated by a water soluble, enteric or enzymatic coating 131.

The shell 130 may be made such that it adds significant additional weight to the capsule device to effectively increase the net SG of the capsule device and shell; or ballast may be included within the shell with the capsule device. In either case, the increased SG can be favorable for reducing transit time through the stomach. After the shell dissolves this additional weight is lost.

Figure 2C:
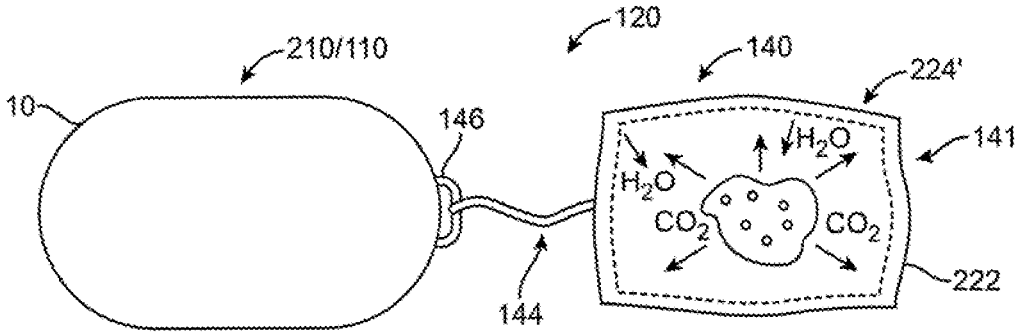

In the case of the shell 130 being made from an enteric material, when the shell and capsule device of FIG. 2A approach the terminal ileum or the cecum, the shell 130 has substantially or entirely dissolved due to the higher pH level. At this point body liquid begins to diffuse through the porous material 222 and enters the pouch 141 interior space. As depicted in FIG. 2C, the diffused body liquid reacts with the effervescent 224 therein to produce CO2. Although a small amount of body liquid resides in the pouch interior, the net effect of the reaction increases the volume of the pouch 140 to a greater extent than the added pouch weight brought on by the body liquid. As a result, the SG of the device in FIG. 2C is less than the SG of the device in FIG. 2A.

Figure 2D:
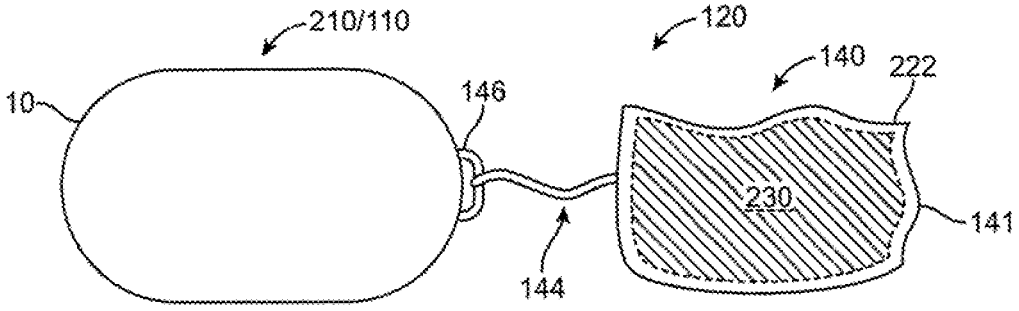

FIG. 2D depicts the state of the device 120 after all or most all of the effervescence has taken place and the CO2 has diffused out of the pouch 141. For example, after about 4 to 12 hours from the start of the reaction producing CO2 the pouch 141 interior contains mostly but limited amounts of water 230 from body liquids, which results in a small increase in the device 120 SG. Eventually the device 120 SG returns to the SG it had prior to the capsule device being placed in the shell 130.

In some embodiments the pouch 140 may be rectangular when deployed, as in the case of FIG. 2C. In other embodiments the pouch may be elliptical, e.g., circular, so that when it inflates with CO2 the pouch has more rounded corners. In some embodiments the pouch 140 may be designed to be more of a hat or a sock on the housing, such as the embodiments described in connection with FIGS. 8A-8C. In some embodiments the shell 130 may completely encapsulate a sensing device and deformable member, or only a portion of the sensing device so as to allow the sensing device to acquire data prior to the deformable member being exposed to body liquid. Any combination of these embodiments is contemplated.

Figure 3A:
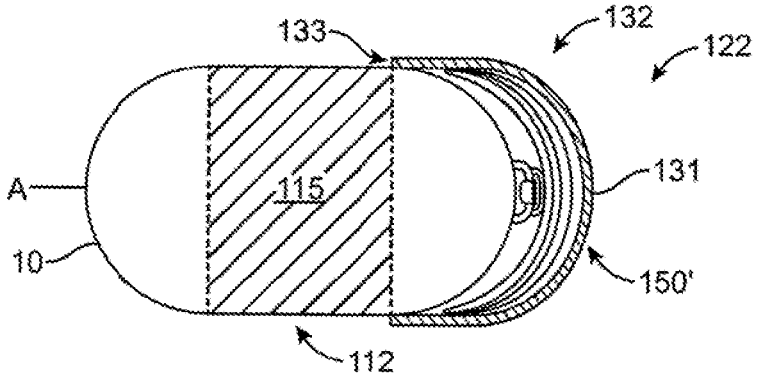
FIGS. 3A through 3B illustrate another embodiment of a capsule device. The pouch of the device is enclosed or encapsulated within a dome in FIG. 3A.
Figure 3B:
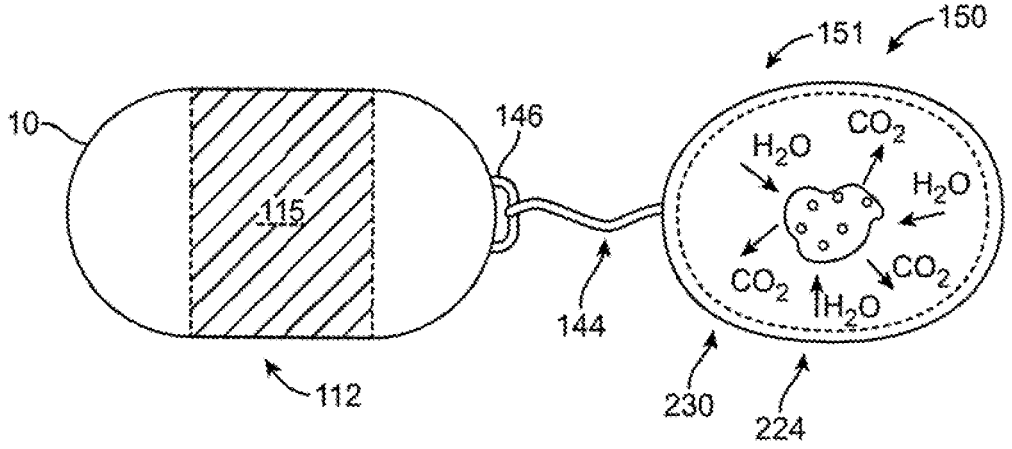

With reference to FIGS. 3A through 3B there is depicted a capsule device 122 including a deformable member 150 tethered to the housing 10 of a sensing system 112 according to another embodiment. FIG. 3A depicts the device 122 with a dome 132 (shown in cross-section) encapsulating the deformable member 150 but not the entire sensing system 112. A sensing system according to this embodiment may be the same as that described for the capsule endoscope in U.S. Pat. No. 8,636,653 (the '653 patent). Referring to the '653 patent, in FIG. 2A there is shown a field of view (FOV)

defining an imaging region 212, which is directed radially outward, as opposed to forwardly with respect to the axis A in FIG. 3A. The shell 130 that encloses the entire device (FIG. 2B) would prevent images from being gathered until the shell 130 has dissolved, since the shell 130 blocks or obscures the FOV for an capsule endoscope configured as in the '653 patent.

Referring to FIG. 3A the sensing system 112 radially-outwardly directed FOV is indicated by the shaded area 115. The dome 132 (enclosing a folded deformable member 150') is sized to not obstruct this FOV for the sensing system 112. By the dome 132 not covering the FOV it is possible for the capsule device 122 to gather images before the dome 132 has dissolved. The dome has a bulbous shape such that the radius of curvature of the bulbous dome may be greater than a radius of curvature of the housing surface it covers. The dome 132 has a straight or cylindrical shaped end 133. The dome 132 may be secured in place by a biodegradable adhesive applied between the end 133 and surface of the housing 10. The dome may alternatively have about the same radius of curvature as the housing surface it covers. In this case the dome 132 may have an elongated cylindrical section 133 sized to provide the space between the inner dome surface and housing surface 10 for the folded deformable member 150'.

Referring to FIG. 3B there is shown the deformable member 150 after the dome 132 has dissolved and the effervescent 224 begins to react with the diffused body liquid. The pouch 151 is shaped as an ellipse, which may be preferred over the rectangular-shaped pouch 141 from FIG. 2B.

By its construction the pouch 140 when at full inflation may tend to form a cylindrical volume but with the seams extending around its perimeter. In the case of the elliptical-shape pouch, the inflated shape may to take the form of a spheroid having the seams. In other embodiments the pouch 140 or 150 may be formed (at least in-part) by a blow-molding or injection molding process, in which case the pouch may more resemble a cylindrical shape or spheroid, respectively.

Figures 4A, 4B, 4C, 4D, 4E:
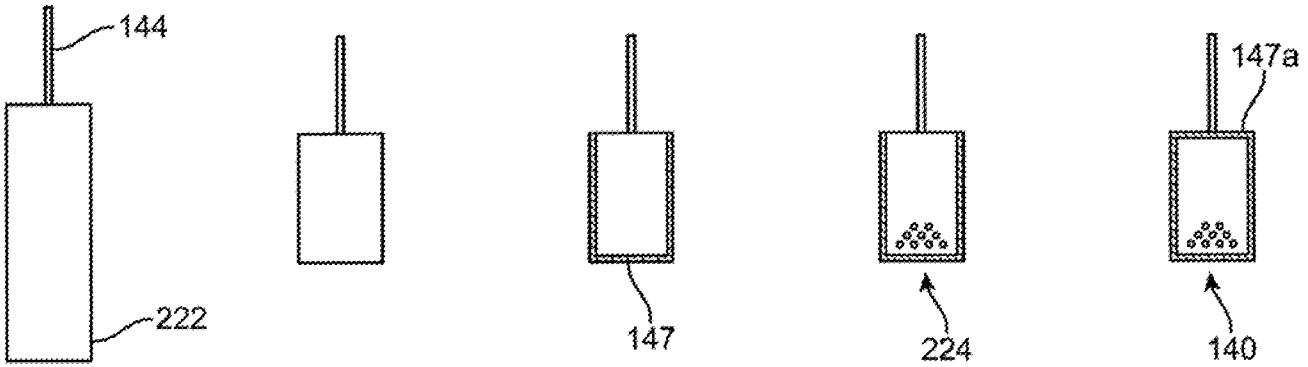
FIGS. 4A-4E illustrate an assembly process for the pouch of FIG. 3A.

FIGS. 4A through 4E depicts an assembly of the deformable member 140. In this example a length of 30 mm is chosen for the tether 144. And membrane material of 60×11 mm selected for the pouch 141 (FIG. 4A). The membrane 222 is folded over to make the 30×11 mm size for the pouch 141 (FIG. 4B). Three sides 147 of the membrane 222 are secured together (FIG. 4C), e.g., by heat seal. The effervescent 224 is added to the pouch 141 (FIG. 4D). The pouch 141 is evacuated of air and heat sealed on the open side 147a, to produce the deformable member 140 of FIGS. 2A-2D. To make the pouch of FIG. 3B a membrane 222 may be cut to have a connected pair of ellipse shapes, so that when folded at the connection part the pouch shape takes the form shown in FIG. 3B.

Figure 5:
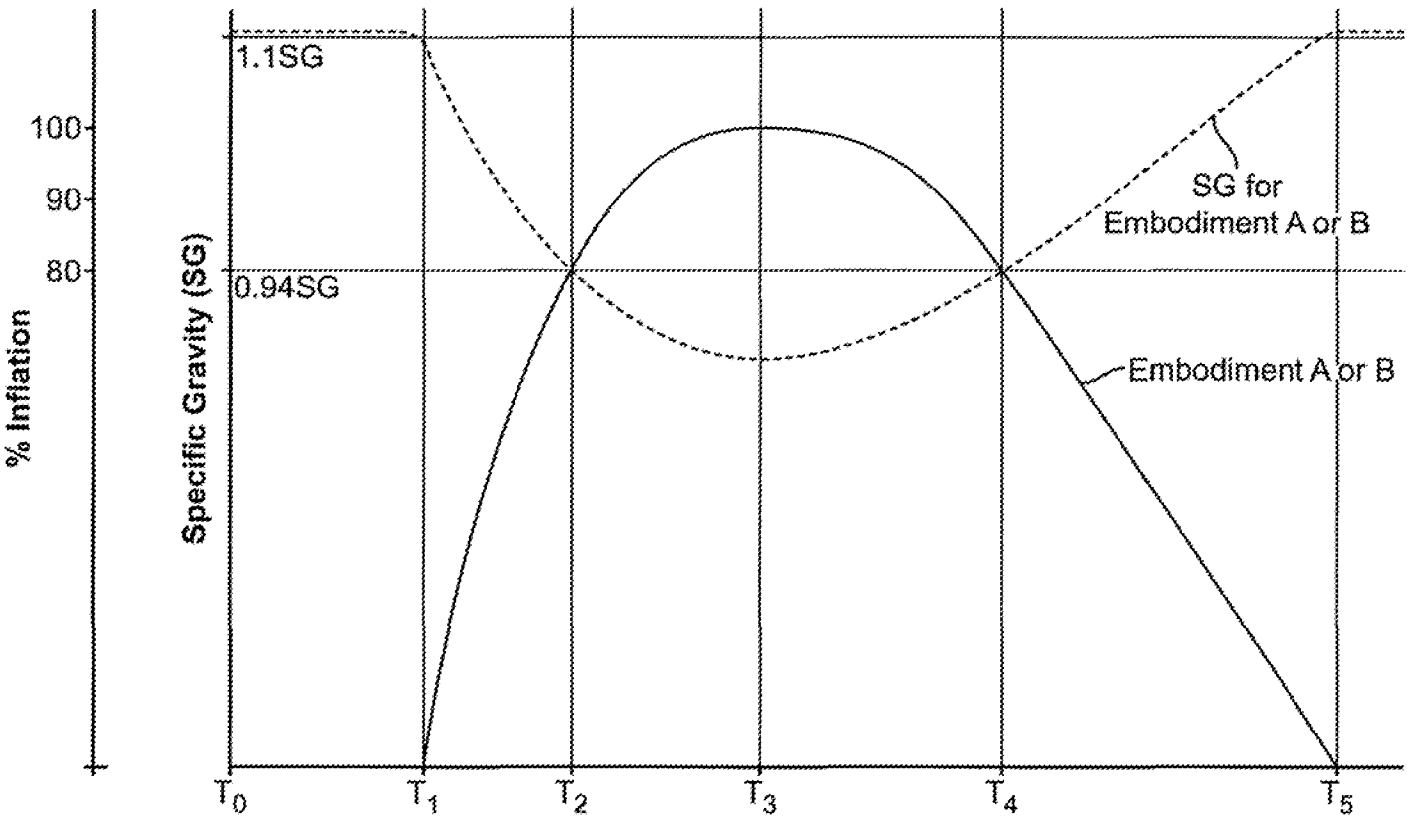
FIG. 5 is a graph showing changes in SG and inflation for pouches of capsule devices according to two embodiments of the disclosure. Shown are plots for a change in SG for a capsule device according to an Embodiment A and an Embodiment B, respectively. The Embodiment A capsule device has no enteric coating, or no shell or dome made from an enteric material when the capsule device is swallowed. The Embodiment B capsule device having an enteric coating, or shell or dome made from an enteric material when the capsule device is swallowed. The abscissa is time (t), where t=T0 represents the time when the capsule device is swallowed or placed or placed in body fluid. There are two ordinates in FIG. 5. The first (leftmost) ordinate refers to the percentage change in inflation for the pouch where 100% inflation means the highest amount of inflation or gas pressure achieved within the interior of the pouch. This ordinate corresponds to the solid curve in the graphs. The adjacent ordinate refers to the capsule device SG and corresponds to the dashed curves. Time t=T1 represents the time when the reaction between the effervescent and water starts to take place. Time t=T2 represents the time when the SG of the device has reached about 1 and is becoming buoyant. SG is above 1 for the period t=T2−T0. The period t=T2−T1 may correspond to a period of between 0.05 to 3 hours. The capsule device has an SG less than or equal to about 1 SG for the period t=T4−T2, which may correspond to a period of between 1 to 12 hours.

With reference to FIG. 5 there is a graph depicting inflation and deflation periods for two types of capsule devices called Embodiment A and Embodiment B, respectively. The Embodiments A and/or B may correspond to any of the illustrated embodiments of a capsule device having deformable members 140 or 150. The solid curves refer to an inflation percentage (verses time) and the dashed curves refer to the change in SG for the Embodiments A and B, respectively. In these graphs the SG values of 0.94 and 1.1 are provided only as examples. As noted earlier, the upper end of SG may be up to 2 and the lower end may be as low as 0.8. Moreover, the inflation percentage (80% and 100%) is exemplary only. In some embodiments the pouch may be constructed so that a desired lower end for SG is reached at only about 70%, or 75% inflation.

TABLE 1A, below, provides one example of a capsule device having the characteristics of Embodiment A. In this example the capsule device has no enteric coating, nor does it have a shell or dome made form an enteric material. Thus, the deformable member of Embodiment A becomes exposed to body liquid relatively soon after the capsule is swallowed, e.g., within 5-30 minutes after being swallowed. According to Embodiment A the deformable member may become exposed to body liquid while the capsule resides in the stomach. Capsule devices according to Embodiment A, which are configured for use without an enteric coating, or enteric shell or dome, have a deformable member that inflates more slowly than capsule devices encapsulated within an enteric coating or material. Embodiment B, in contrast, has a faster rise time. In the preferred embodiments the balloon is configured so that when it reaches about 80% inflation the capsule SG is equal to or less than 1.

TABLE 1A (Embodiment A)

| Time point/ interval FIG. 5 | Approximate time after swallowing (hours) | Approximate location for patients | Comment |
|---|---|---|---|
| T0 | n/a | Mouth | Capsule SG >1; camera capsule with attached ouch encased in soluble sphere or dome |
| T1 | 5-30 min | Stomach | Outer sphere or dome dissolved and camera capsule with attached pouch comes in contact with body fluids. Capsule SG starts to decrease as water permeates the pouch and initiates reactions with effervescent within. CO2 is generated. |
| T2 | 1-4 hours | small intestine | Capsule SG becomes <1 and enough CO2 gas has been produced to make the device bouyant. |
| T1 ≤ t ≤ T2 | 1-4 hours* | n/a | CO2 gas generation is slow enough to prevent the device from becoming bouyant and trapped in the stomach |
| T3 | n/a | Large intestine | Capsule SG <1; SG is lowest, CO2 volume and gas pressure as gas diffuses through membrane wall faster than it is produced. |
| T4 | 3-15 hours | Large intestine | Capsule SG becomes >1; CO2 gas has diffused through membrane wall and the device is no longer bouyant |
| T2 ≤ t ≤ T4 | 4-12 hours* | n/a | Capsule SG <1; Device is bouyant and SG is below 1 for at least 4 hours to make sure the device transits well from small intestine to lage intestine. |
| T5 | 4-25 hours | Excreted or in large intestine | >90% of the generated CO2 gas has diffused out of the pouch |

*Does not reflect the times from swallowing the device

TABLE 1B (Embodiment B)

| Time-point FIG. 5 | Approximate time after swallowing (hours) | Approximate location for most patients | Comment |
|---|---|---|---|
| T0 | n/a | Month | Capsule SG >1; camera capsule with attached pouch encased in soluble sphere or dome |
| T1 | 10 min-3 hours | Small intestine | Outer sphere or dome w euteric or time controlled coating dissolved and camera capsule with attached pouch comes in contact with body fluids. Capsule SG starts to decrease as water permeates the pouch and initiates reaction with effervescent within and CO2 starts to be generated. |
| T2 | 30 min-3.5 hours | Small intestine | Capsule SG becomes <1 and enough CO2 gas has been produced to make the device bouyant. |
| T1 ≤ t ≤ T2 | 5 min-1 hour | n/a | CO2 gas generation can be fast as the device is already in small intestine and the risk that the device becomes bouyant and trapped in the stomach is low. Allows for thinner pouches. |
| T3 | n/a | Large intestine | Capsule SG <1; SG is lowest. CO2 volume and gas pressure at highest and begins to decrease as gas diffuses through membrane wall faster than it is produced |
| T4 | 3-15 hours | Large intestine | Capsule SG becomes >1; CO2 gas has diffused through membrane wall and the device is no longer bouyant. |
| T2 ≤ t ≤ T4 | 2-15 hours* | n/a | Capsule SG <1; Device is bouyant and SG is below 1 for at least 2 hours to make sure the device transits well from small intestine to large intestine. |
| T5 | 4-25 hours | Excreted or in large intestine | >90% of the generated CO2 gas has diffused out of the pouch |

*Does not reflect the times from swallowing the device

TABLE 1B, below, provides one example of a capsule device having the characteristics of Embodiment B. In this example the capsule device has an enteric or time-controlled coating, or has a shell or dome made from an enteric or time-controlled material. Thus, the deformable member of Embodiment B becomes exposed to body liquid after the capsule has passed through the pyloric valve. According to Embodiment B the deformable member does not become exposed to body liquid until the capsule reaches the small bowel (Once the enteric or time-controlled coating has dissolved the body fluid dissolvable shell or dome dissolves quickly). Capsule devices according to Embodiment B have a deformable member that inflates more quickly than capsule devices encapsulated without an enteric or time-controlled coating or material (Embodiment A). Referring once again to FIG. 5, the different curves and/or slopes of curves for the pouch inflation pressure vs. time, and/or percent inflation for a target SG to achieve buoyancy, may be arrived at by varying parameters affecting the inflation rate and duration for the pouch when exposed to body liquid. These parameters may include one or more, or any combination of the following parameters (a) through (i):

(a) The amount (by weight or volume) of effervescent in the pouch. In one embodiment between about 1 and 100 milligrams, and more preferably between about 5 to 50 milligrams of an effervescent comprising a bicarbonate salt an anhydrous acid or preferably, sodium bicarbonate, and/or potassium bicarbonate, and anhydrous citric acid is used. In a preferred embodiment the effervescent is composed of about 20% by weight of sodium bicarbonate, about 40% by weight of potassium bicarbonate, and about 40% by weight anhydrous citric acid.

(b) Coarse or fine granules of effervescent or an effervescent tablet. And/or aged or fresh granules of effervescent or an effervescent tablet.

(c) The amount of desiccant in the pouch vs. effervescent. In one embodiment a ratio of between about 1:25 and 1:0.04 of desiccant to effervescent, and more preferably between about 1:10 and 1:0.1 of desiccant to effervescent is used. In a preferred embodiment polyethylene glycol is used as a desiccant and the ratio of effervescent to this desiccant is 0.5 to 2, or 1 to 1. A preferred molecular weight of the polyethylene glycol is in the range of 5,000 to 50,000 Daltons with a linear, 4- or 8-armed star structure.

(d) The presence of a coating over the effervescent, e.g., an enteric coating or water soluble coating. In some embodiments it may be desirable to coat the effervescent material with a coating so as to obtain a more controlled release of CO2. The effervescent may be coated with an enteric coating, to be used in combination with a shell or dome that dissolves in the stomach. In some embodiments it may be desirable to have the effervescent placed in contact with the membrane of the deformable member so that body liquid diffused through the membrane will reach and react with the effervescent material as quickly as possible. In other embodiments it may be unnecessary or undesirable to place the material in contact with the membrane because it is desirable to delay the reaction time for reasons previously given above.

(e) The pouch size. In one embodiment a rectangular pouch has dimensions of about 30×11 mm or about 2×330 $mm^2$ surface area total surface area for the outer surface of membrane material. A rectangular pouch (FIG. 2A) may have a ratio of length to width of 2:1, 1:1, or 3:1, or between 2:1 to 3:1 for the membrane. The pouch may alternatively have an elliptical shape (FIG. 3B). In the embodiments the total external surface area of the pouch (representative approximately of its internal volume capacity when under pressure) is between 50 and 1,500 $mm^2$ and more preferably between 300 and 1,000 $mm^2$.

(f) The membrane wall thickness. The wall thickness can range from between 0.2 to 10 mils (about 5 to 254 microns) and more preferably 0.5 to 5 mils (about 12 to 125 microns).

(g) The membrane may be made from any of the following, or combinations of material: polyetherblockamide copolymers, thermoplastic polyurethanes, polyamides, polyamide block copolymers, polyamide elastomers, polyurethanes, polyesters, polyester copolymers, polyamide copolymers, polyurethane copolymers, polyether copolymers, polyesteramides, polyesteramide copolymers, polyvinyl chloride, polyvinyl chloride copolymers, polyvinylidene dichloride, polyvinylidene dichloride copolymers, fluoropolymers, polyvinyl fluoride, polyvinyl fluoride copolymers, polyvinylidene difluoride, polyvinylidene difluoride copolymers, polyvinylpyrrolidone copolymers, polyvinylalcohol copolymers, two layered, three layered, or multi layered films of various materials may be used to provide a combination of barrier properties from one material and mechanical or adhesive properties for sealing of another. Pouches may also have one material on one side and another material on the other or opposite side. The membrane material may be present on the entire side, or only a portion of one side, or only exposed on a portion of one side or both sides. Additionally, the membrane composition may be varied by thickness, polymer type, layering of different or the same material, or by change of patterning.

(h) An enteric, enzymatic, time-controlled (water soluble), or body fluid-soluble (water-soluble, non-enteric) coating.

(i) An enteric, enzymatic, time-controlled (water soluble), or body fluid-soluble (water-soluble, non-enteric) shell or dome.

With respect to parameter (a), the more effervescent material in the pouch, the more CO2 gas is available for inflating the pouch. The amount of effervescent chosen may be based on the desired amount and duration of buoyancy for the capsule. For example, referring to FIG. 5 the duration of time for Embodiment A at or above 80% inflation covers the period T2 to T4. During this time the capsule has an SG no greater than 1. Thus, for this embodiment it can be expected that the capsule will float in the body liquid from T2 to T4. If a greater amount of effervescent is added the duration of time where SG is less than 1 may increase.

With respect to parameter (b), the coarseness of the effervescent particles, or choice of a tablet over particles for the effervescent may change the reaction times, e.g., production of CO2 at a quicker rate when finely ground effervescent particles are used in place of a tablet due to the increased surface area. In current testing however it was found that the size of the effervescent granules, or choosing a granule over a tablet did not produce much change in the curves of FIG. 5.

With respect to parameter (c), the addition of desiccant to the pouch can significantly delay or reduce the rate of CO2 production in the pouch, because the desiccant will adsorb water, or absorb water depending on the desiccant used (both types are contemplated for use). Accordingly, by using a greater percentage of desiccant material (in proportion to effervescent) the rise time for pouch inflation can be increased. For example, all other parameters being equal between Embodiments A and B, the Embodiment A curve (FIG. 5A) may be achieved by adding more desiccant to the pouch of Embodiment B (FIG. 5B), thereby making the rise time longer for Embodiment A than Embodiment B. A slower rise time is preferred for a shell, dome or coating that dissolves in the stomach.

Thus, with respect to parameters (b) and (c), the addition of desiccant inside the pouch will adsorb (or absorb) the water from the body liquid and delay production of CO2 and the coarseness of the desiccant particles, or choice of a tablet over particles for the effervescent combined with the desiccant may change the reaction times, e.g., production of CO2 at a slower rate when finely ground and well mixed as a powder or tablet effervescent and desiccant particles are used in place of a more coarse or less well mixed mixture due to the increased surface area.

With respect to parameter (d), the coating on the effervescent particle (or tablet) may prevent or delay the body liquid mobilization of the effervescent material and therefore may delay the production of CO2 until the right time or the pH has changed. The coating thus can effectively reduce the rate of CO2 production within the pouch and increase the rise time. In some embodiments an effervescent has an enteric coating. Other embodiments use instead a coating designed to dissolve in the stomach or small bowel within about 2-4 hours after being in contact with body fluids, unless they are enteric, in which case they will not dissolve in the low pH of the stomach but disintegrate in the higher pH environment of the small bowel or colon. The coating may be made of polymers, polysaccharides, plasticizers, methyl cellulose, gelatin, sugar, or other materials. Hydroxypropylcellulose, hypromellose acetate succinate and methacrylic acid co-polymer type C are examples of an enteric polymer. These materials may also be applied as coatings to the deformable member alone or to it and the sensing system. For example, all other parameters being equal the Embodiment A curve (FIG. 5A) may be achieved by using a non-coated effervescent, while using a coated effervescent material may delay the onset of T1 from being in the stomach to being in the small bowel (Embodiment B, FIG. 5B) or if time controlled may delay it from 20 min after swallowing to 2-4 hours after swallowing. A delayed T1 is preferred for a shell or dome that dissolves in the small intestine. It also allows the use of thinner balloon materials.

With respect to parameter (e), pouch sizes may be limited to ensure that it does not get caught on any anatomy when the pouch becomes inflated, e.g., if the pouch were to achieve near 100% inflation prior to reaching the cecum. A smaller pouch size for the same amount of effervescent should produce a higher gas pressure, which may increase the rate of diffusion of gas from the membrane. In some embodiments a more non-compliant membrane is used, as a measure for controlling the volume of the inflated pouch. A compliant membrane material may be used, as a measure for controlling internal pressure. A less or more compliant membrane material may be understood as a membrane having a lower or higher wall thickness, respectively, or a lower or higher elastic modulus in general.

With respect to parameters (f) and (g), the pouch membrane material and wall thickness can affect the rate of diffusion of body liquid (water) into the pouch interior and as a result the rate of CO2 production, parameters (f) and (g) also affect diffusion of CO2 gas out of the pouch. For example, if the membrane wall thickness is increased, the rate at which body fluid diffuses into, and/or CO2 gas diffuse out of the pouch interior should decrease. As will be appreciated from the foregoing, this effect may be somewhat different if, for example, at the same time the amount of effervescent used per unit volume of the pouch interior is increased or decreased. If there is more gas produced per unit volume the pouch internal gas pressure should increase, which may decrease the diffusion of body fluid into the pouch thereby increasing the buoyancy period and/or increasing the rise time.

Similarly, for a higher wall thickness the deflation period (e.g., from T4 to T5 in FIG. 5B) should increase. An increase or decrease in the surface area of the pouch may be thought of as having a similar effect as a decrease or increase, respectively, in the effervescent per unit volume. For example, for an increase in the surface area with no increase in the amount of effervescent used the rise time should decrease.

With respect to parameters (h) and (i), embodiments of a capsule device have an enteric coating, or shell or dome made from an enteric material, or the capsule device may be coated with an enteric, enzymatic, time-controlled (water soluble), or body fluid-soluble (water-soluble, non-enteric) coating, or use shells or domes devoid not made from an enteric material. FIGS. 5A and 5B and Tables 1A and 1B illustrate these differences. The foregoing selection of appropriate parameters to achieve a desired inflation rate may be guided substantially by whether or not an enteric coating or material is used. Embodiments of coatings, domes or shells are designed to dissolve in the stomach or small bowel within about 30 minutes of swallowing, unless they are enteric, in which case they will not dissolve in the low pH of the stomach but disintegrate in the higher pH environment of the small bowel or colon. The shell or dome may be made of polymers, polysaccharides, plasticizers, methyl cellulose, gelatin, sugar, or other materials. Hydroxypropylcellulose, hypromellose acetate succinate and methacrylic acid copolymer type C are examples of an enteric polymer These materials may also be applied as coatings to the deformable member alone or to it and the sensing system. There may be reasons for using one type of dome, coating or shell over another depending on the type of application. On the one hand a shell configured to dissolve in the stomach is reliable and should not depend too much on the patient's condition. On the other hand, there may be concern over whether the pouch inflates too soon and before the capsule has passed through the stomach. In this case the capsule may not exit the stomach and instead float in the stomach.

An enteric shell or an enteric coated shell should not dissolve fully until the capsule has reached the small bowel. Thus, the pouch should ideally not start to inflate until after the capsule has passed through the stomach. The advantage here is the pouch may inflate rapidly and the only possible limitation or challenge may be to keep pouch inflated long enough to stabilize its transit through the ascending colon as well as through the transverse colon. Another advantage is that more types and/or thinner pouch materials may be used. And there is less need for desiccants. However, an enteric shell or coating can be expensive and more sensitive to changes in pH. Thus, the enteric shell may not fully dissolve in the small bowel unless the pH level is sufficiently high, which can make its effectiveness more dependent on a particular patient's condition. Should the shell not dissolve, the pouch cannot inflate and the capsule will not ascend the colon.

Thus, when choosing between an enteric shell, dome or coating verses one that is dissolved by gastric juices, one may select a pouch configuration that has a slower rise time when the shell, dome or coating dissolves in the stomach. And when an enteric shell, dome or coating is used the rise time can be decreased. There may be advantages or disadvantages, and/or other factors to consider. For instance, a configuration that yields a slower rise time may also take longer to deflate, which can result in unacceptable delay in getting the capsule through the transverse and descending colon due to its low SG. This problem may be overcome by using a relatively thin wall thickness, since tests show that the deflation time is mostly a function of the wall thickness of the membrane.

Testing

Bench tests were conducted to evaluate changes in buoyancy periods for a variety of pouch configurations. The tests varied the amount of effervescent material, the pouch material, pouch wall thickness and dimensions, as well as the type and amount of desiccant. The apparatus used to test pouch properties consisted of a pouch (assembled as shown in FIGS. 4A-4E) suspended from an arm coupled to a weighing scale. The arm overhung a basin of water heated to about 37° C. Ballast was attached to the pouch. The weight of the suspended pouch and ballast were recorded (dry weight). Next, the pouch and ballast and were dropped into the water. The change in weight of the pouch and ballast were then recorded over the next 10 to 20 hours.

As the reaction between the water and effervescent takes place, the SG of the pouch and ballast changed: the SG decreased ($CO_2$ produced from the reaction between the water and effervescent), the SG reached a minimum value (corresponding to a 100% inflation condition), and then the SG increased as $CO_2$ diffused from the pouch.

Figure 6:
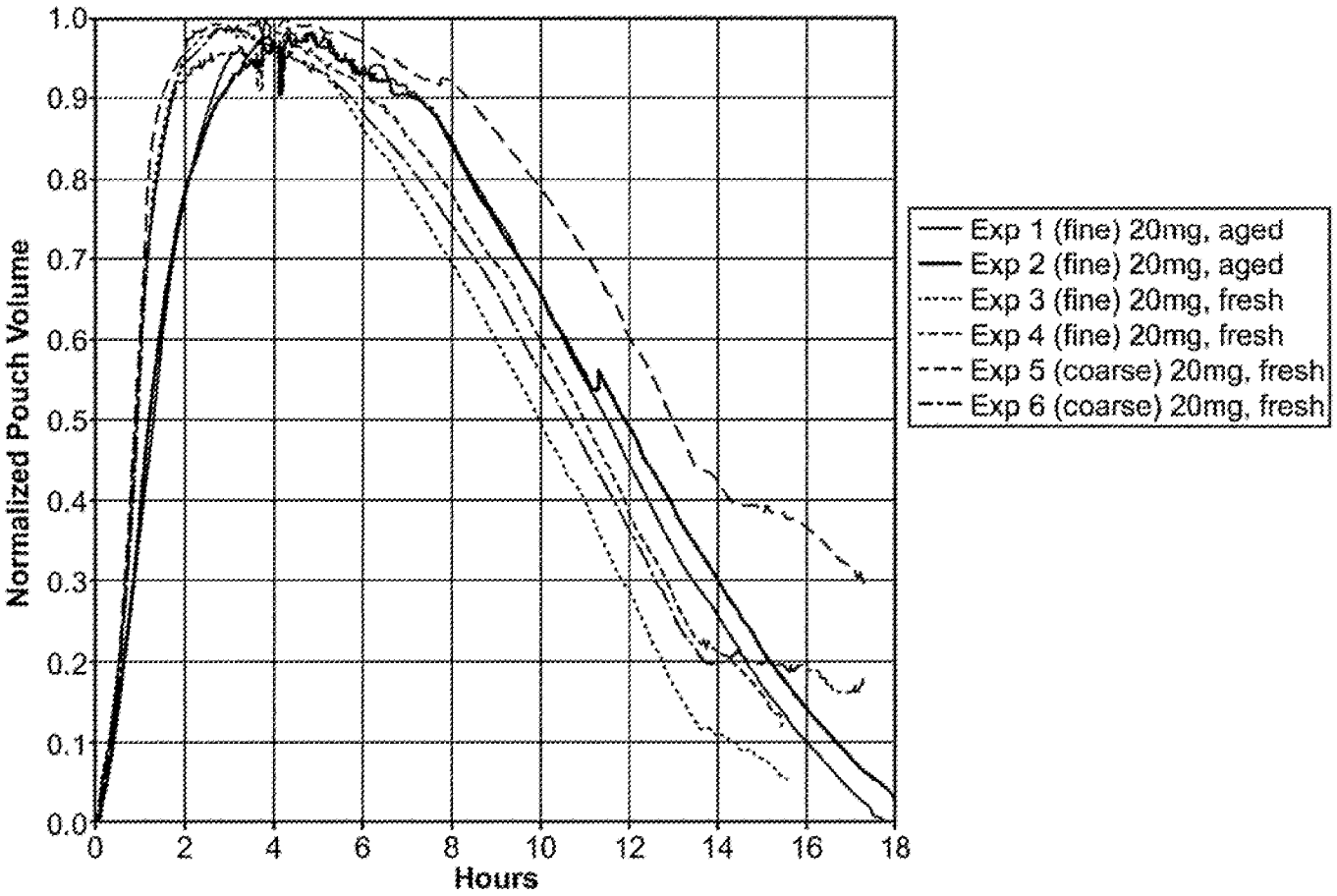
FIG. 6 is a plot showing changes in pouch inflation over time among six different configurations of a pouch containing an effervescent. The ordinate refers to a normalized inflation amount where "1" means the highest amount of inflation or volume increase for the respective pouch.

FIG. 6 is a normalized plot showing changes in pouch inflation volume over time among six different configurations of a pouch from the bench tests. The ordinate refers to the percentage change in inflation for the pouch where 100% inflation means the highest amount of inflation or gas pressure achieved within the interior of the pouch. The test article for each of the six test samples depicted in FIG. 6 (labeled as "Exp 1", "Exp 2", "Exp 3", "Exp 4", "Exp 5" and "Exp 6") are summarized below:

Exp 1: a pouch membrane was made from PEBAX 4 mils and with dimensions 30×11 mm, wall thickness 4 mil (0.1 mm), and 20 mg of effervescent used (fine grind, aged).

Exp 2: a pouch membrane was made from PEBAX 4 mils and with dimensions 30×11 mm, wall thickness 4 mil (0.1 mm), and 20 mm of effervescent used (fine grind, aged).

Exp 3: a pouch membrane was made from PEBAX 4 mils and with dimensions 30×11 mm, wall thickness 4 mil (0.1 mm), and 20 mg of effervescent used (fine grind, fresh).

Exp 4: a pouch membrane was made from PEBAX 4 mils and with dimensions 30×11 mm, wall thickness 4 mil (0.1 mm), and 20 mg of effervescent used (fine grind, fresh).

Exp 5: a pouch membrane was made from PEBAX 4 mils and with dimensions 30×11 mm, wall thickness 4 mil (0.1 mm), and 20 mg of effervescent used (coarse grind, fresh).

Exp 6: a pouch membrane was made from PEBAX 4 mils and with dimensions 30×11 mm, wall thickness 4 mil (0.1 mm), and 20 mg of effervescent used (coarse grind, fresh).

FIG. 7 shows additional results from tests. Listed are the materials and size and wall thickness of the pouch. The amount of effervescent used was varied from between 5 mg to 30 mg and was either coarse or fine, and aged or new. The "n" vales refer to the number of experiments performed. The data under the columns Ta, Tb, Tc, Td, Te and Tf are explained below (time "T0" refers to the moment when the pouch is placed in the water). These times are given in units of hours.

Ta is the time elapsed from T0 to when the pouch reaches 80% inflation.

Tb is the time elapsed from T0 to when the pouch reaches 100% inflation.

Tc is the time elapsed from T0 to when the pouch inflation begins to decrease from a 100% inflation state.

Td is the time the pouch maintains 100% inflation; thus, Td=Tc−Tb.

Te is the time elapsed from T0 to when the pouch inflation begins to decrease from a 80% inflation state.

Tf is the time the pouch maintains 80% inflation; thus, Tf=Te−Ta.

In some cases the pouch did not reach 100% inflation or 80% inflation. These are noted in the comments. In some cases the rectangular-shaped pouch was modified to have a double seal or a double bag. A double seal means there was an inner rectangular seal made in the bag, in addition to the outer seal. A double bag means the effervescent was placed in a sealed inner bag, and then the inner bag was placed in a sealed outer bag.

The parameters that have the most significant effects on the inflation/deflation periods reported are the type of polymer, wall thickness, type and amount of desiccant, and quantity of effervescent material in the pouch. When more effervescent was used, the rise time decreased and the period above 80% inflation increased. An increase in effervescent material used, however, can also significantly increase the deflation time.

The following discloses additional embodiments of a capsule device.

Figure 8A:
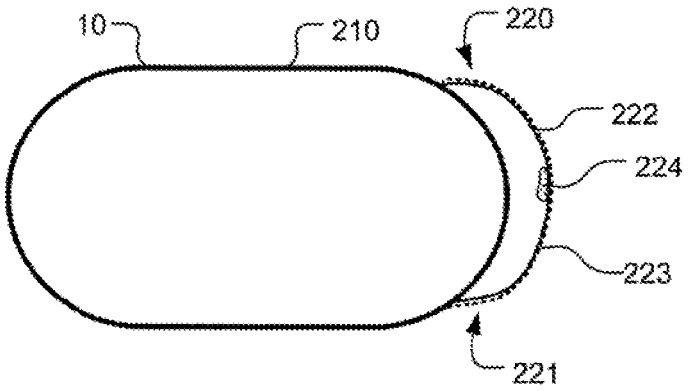
FIGS. 8A-8E illustrate an example of various specific gravity or density states for a capsule device incorporating density control.
Figure 8B:
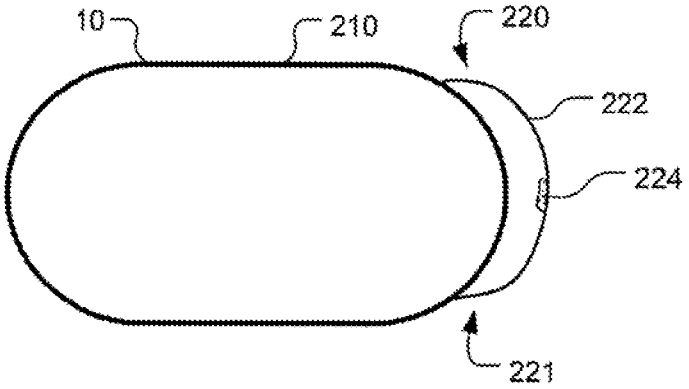
Figure 8C:
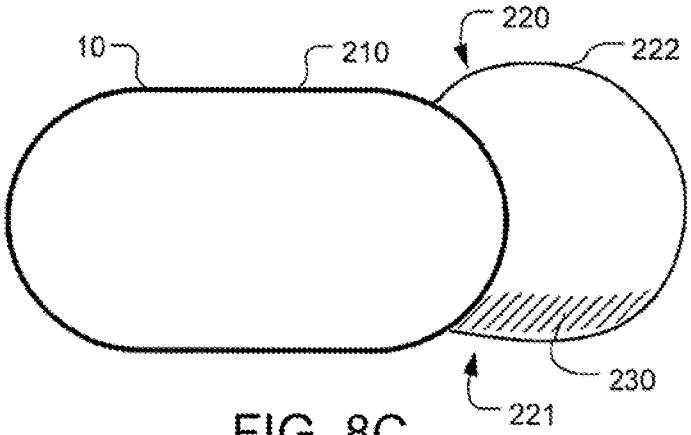

FIGS. 8A-8C depict an example of a capsule device with a deformable member 220 integral with the housing 10 of the sensing system 110. As in prior embodiments the device includes a pouch 221 formed from a semi-permeable membrane material 222, and an effervescent 224 contained within an interior of the pouch 221. One difference between this capsule device and previously discussed embodiments is that the deformable member 220 is integral with the capsule housing 10, as opposed to being tethered to it. The membrane material 222 chosen may be more elastic than in prior embodiments since ends of the pouch 221 is constrained to the relatively rigid surface of housing 10 and thus less able to increase its interior volume as in prior embodiments without stretching of the membrane. The membrane material 222 may be attached to the surface of the housing 10 by an adhesive so that a fluid-tight interior to the pouch 221 is formed. As such, body liquid enters the interior of the pouch 221 only by way of diffusion through pores of the membrane 222.

FIG. 8A depicts a capsule device before the deformable member 220 expands in response to the effervescent 224 being exposed to body liquid. The effervescent 224 is contained within the interior of the pouch 221 made of the porous or semi-permeable membrane material 222.

In this particular embodiment an enteric coating 223 (as represented by dashed lines) is applied to the exterior of the membrane 222 to prevent diffusion of body liquid into the pouch interior until after the capsule device has entered the small intestine. The enteric coating may also cover the sensing device 110.

Figure 8D:
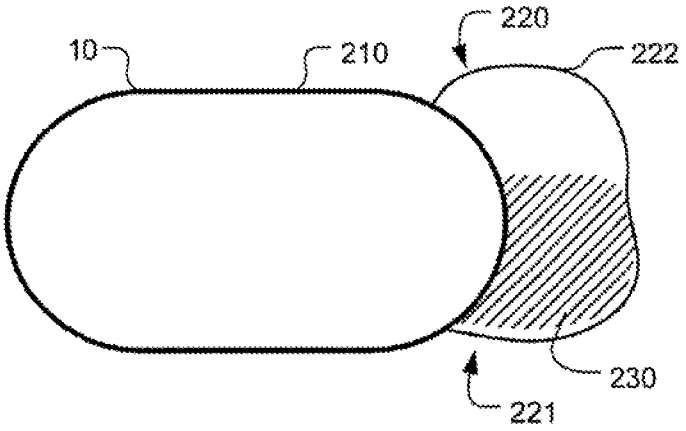
Figure 8E:
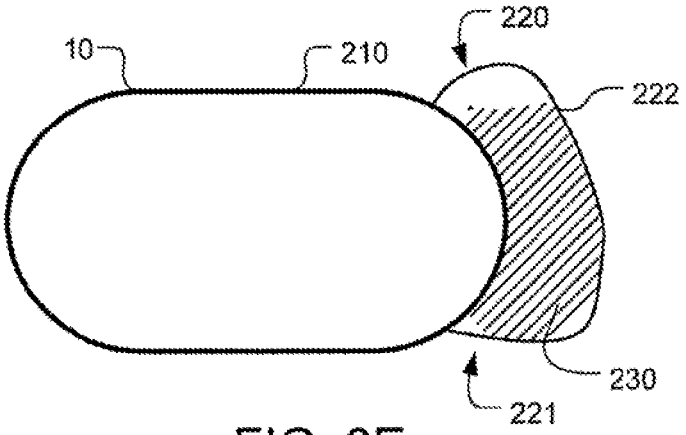

When the capsule device of FIG. 8A approaches the terminal ileum or the cecum, the enteric coating 223 dissolves due to the higher pH level, as depicted in FIG. 8B. With the enteric coating dissolved, body liquid begins to diffuse through the porous material 222 and enters the interior space. Thus, the reaction takes place producing the gas that expands the pouch volume, as shown in FIG. 8C. Although a small amount of fluid 230 resides in the pouch 221 interior, the net effect of the reaction increases the volume of the pouch to a greater extent than the added pouch weight brought on by the body liquid. The SG of the device in FIG. 8C is less than the SG of the device in FIG. 8A. In some embodiments it may be desirable to have the effervescent material 224 placed in contact with the semipermeable membrane of the deformable member so that body liquid diffused through the membrane will reach and react with the effervescent material 224 as quickly as possible. In other embodiments it may be unnecessary or undesirable to place the material 224 in contact with the membrane because it is desirable to delay the reaction time for reasons previously given above FIGS. 8D-8E depict later stages of the capsule device of FIG. 8C Compared to the state in FIG. 8C, the state in FIG. 8D shows that more body liquid has accumulated in the pouch 224 interior and less gas (as a result of diffusion of the gas through the membrane 222). FIG. 8E depicts a state of the capsule device after its SG has increased to above 1 due to the amount of body liquid that has diffused into the pouch 224 interior.

Figure 9A:
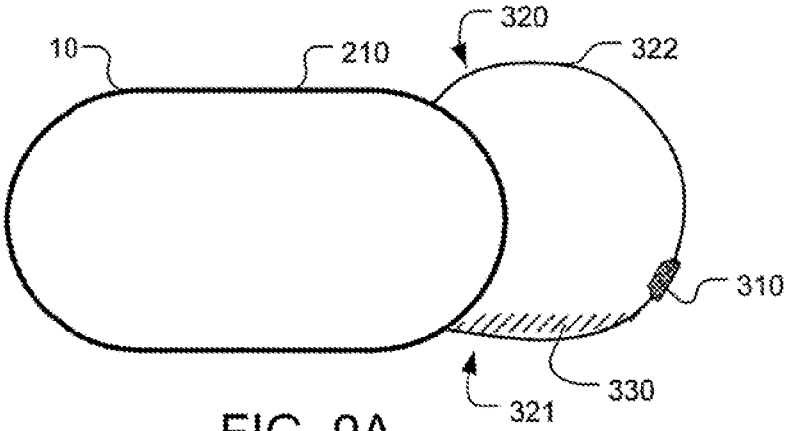
FIGS. 9A-9B illustrate an example of various specific gravity or density states for a capsule device incorporating a biodegradable plug.
Figure 9B:
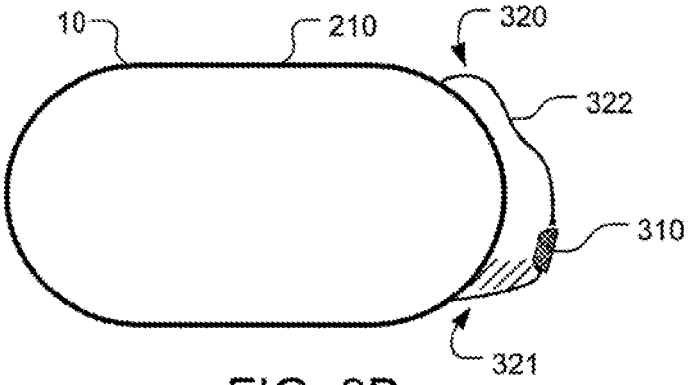

FIGS. 9A-9B depict an example of a deformable member 320 integral with the housing 10 (as in FIGS. 8A-8C). According to this embodiment the deformable 320 includes a pouch 321 having the effervescent in its interior (FIG. 9A shows the pouch 321 configuration after body liquid has diffused into its interior space and CO2 gas released). The pouch 321 is formed by a membrane 322 that is permeable to body liquid and substantially impermeable to gas. A biodegradable relief valve, plug or seal made of a biodegradable (or resorbable) material 310 covers an opening in the membrane 322. The seal 310 may be configured to degrade within a few hours of exposure to body liquid.

Figure 10:
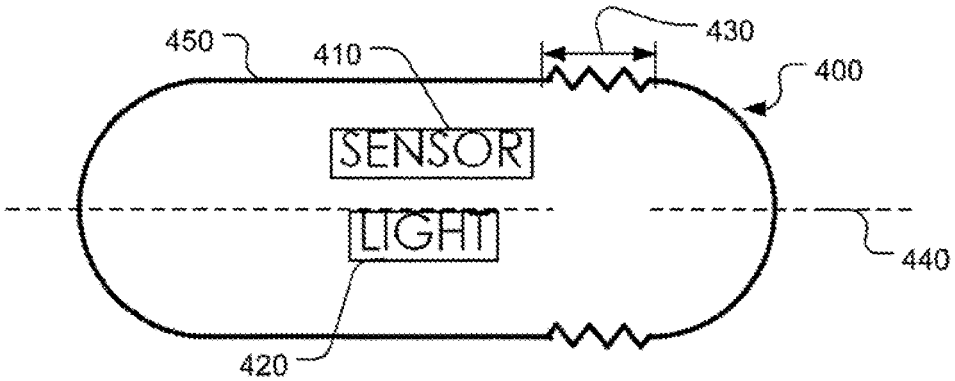
FIG. 10 illustrates an example of a capsule device incorporating density control according to an embodiment of the present invention, where the housing includes a flexible section to expand or contract.

FIG. 9B depicts the state of the deformable member 320 after the seal has degraded. The gas has been released and the SG of the capsule device has increases back to above 1. FIG. 10 depicts an embodiment of a capsule device where a housing 450 of the capsule device 400 includes a flexible section 430. For example, a bellows-like structure can be used for the flexible section. The flexible section can be expanded or compressed along a longitudinal direction 440 of the capsule device 400. Furthermore, the capsule device 400 comprises sensor 410 and light 420 for capturing images inside the body lumen.

Figure 11A:
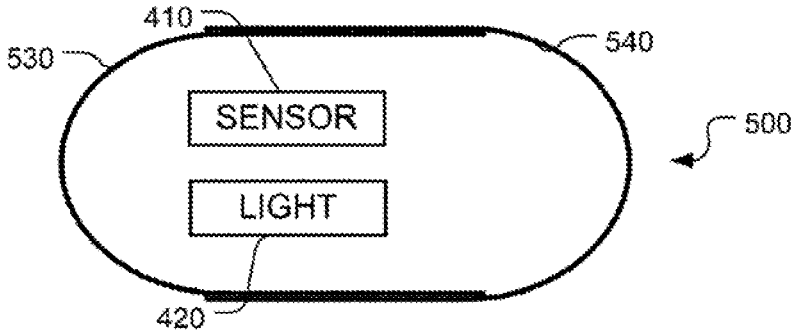
FIGS. 11A-11B illustrate an example of a capsule device incorporating density control according to an embodiment of the present invention, where the housing comprises two closely coupled parts.
Figure 11B:
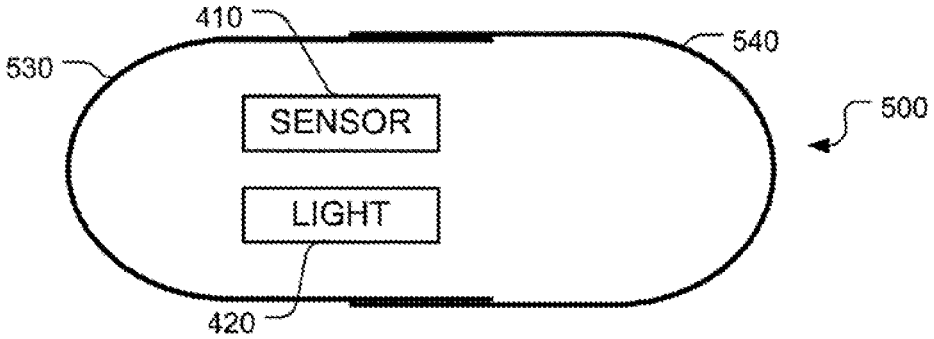

FIGS. 11A and 11B depict an embodiment of a capsule device 500 where two coupled parts 530 and 540 are biased to spring apart to form an enlarged volume of the housing (FIG. 5B). The parts 530, 540 are held together by a biodegradable or resorbable seal. When exposed to body liquid the seal breaks and the two parts move apart. With the increased volume and the housing formed by parts 530, 540 moved apart and the housing being liquid impermeable, the device 500 has a SG that decreases as the parts 530, 540 move part. The housing may be maintained in a sealed (liquid impermeable) condition by disposing an O-ring or gasket between the overlapping sections of parts 530, 540. FIGS. 11A and 11B illustrate states where the capsule device has an SG greater than 1 and less than 1, respectively.

Figure 12:
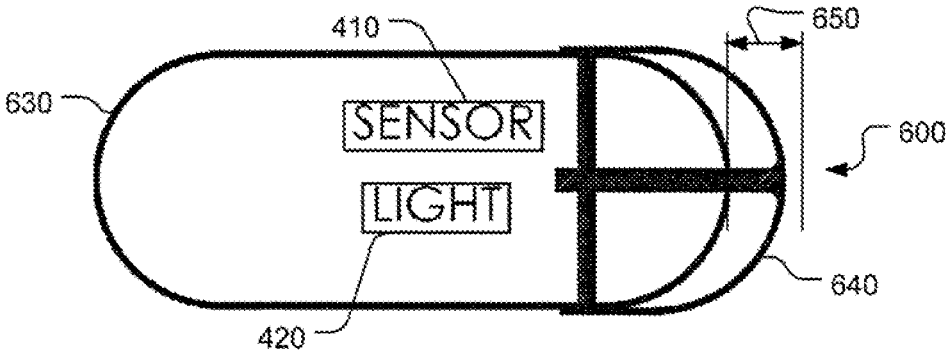
FIG. 12 illustrates an example of a capsule device incorporating density control according to an embodiment of the present invention, where an extendable part is attached to the sensor system.

FIG. 12 illustrates a capsule device 600 where a main sensor system 630 is configured to accommodate an extendable attachment 640. The extendable attachment 640 can be moved within a range indicated by 650. When fully extended (i.e., attachment 640 moved from left to right in FIG. 12) the capsule volume increases; hence the SG decreases.

The embodiments of FIGS. 10-12 illustrate examples of capsules with an expandable housing. The housing may be expanded in these embodiments by an actuator such as a motor and screw drive internal to the housing. Such actuators may consume excessive power, however. Another option is to spring load the housing internally. The housing expansion may be constrained by an external biodegradable shell or coating that dissolves after the capsule device is swallowed.

In one or more of the aforementioned other embodiments a capsule device may be coated with a material to decrease drag or friction between the housing and body liquid, or anatomy encountered in the GI track. Hydrophilic coatings are one example of a coating that may be used to coat the capsule's housing surface.

In a wireless application, a transmitter is used to transmit image data to a receiver system external to the body and the image data is stored in an external recorder. In U.S. Pat. No. 5,604,531, a wireless capsule system is disclosed and the capsule system with a wireless transmitter is powered by the battery within the capsule. For colon applications, the transit time is substantially longer than for small bowel applications. Therefore, the receiver system and external recorder may become burdensome to carry over long hours (e.g., 10 hours or more). Since the time period for a colon application in general takes longer than, e.g., 8-10 hours, an out-patient procedure would require the patient to bring the receiver/transceiver equipment with him or her. This increases healthcare costs since additional (portable) equipment is needed to gather data for the colon. Additionally, the signals transmitted/received between the device and receiver can interfere with nearby equipment, such as another implant. It may therefore be preferred to utilize for colon applications a capsule device that can travel through the large intestine more rapidly. This may be achieved by having the SG return back to an SG greater than 1 after the capsule has passed through the ascending colon, by use of an booster protocol, or a combination of the two. In yet another embodiment of the present invention, the density control means is applied to a capsule system with on-board storage. Such system is disclosed in to U.S. Pat. No. 7,983,458, entitled "in vivo Autonomous Camera with On-Board Data Storage or Digital Wireless Transmission in Regulatory Approved Band", granted on Jul. 19, 201. The capsule system with on-board storage does not require the patient to wear any external equipment. Therefore, the capsule system with on-board storage is much preferred for procedure requiring a prolonged time period. Furthermore, in PCT Patent Application No. PCT/US13/42490, a docketing station to read out archived data from a capsule system with on-board storage is disclosed. The capsule system comprises a set of probe pads disposed on the housing. After the capsule device is excreted and recovered, the image data can be retrieved by probing these probe pads without opening the capsule housing. Since the battery power is pretty much depleted when the capsule device is retrieved, one pair of the probe pads can be used to provide power and ground for the data retrieval operation. Alternatively, the power can be provided using inductive powering as disclosed in PCT Patent Application Series No. PCT/US13/39317. After the capsule is recovered, the data may be transmitted optically through a transparent portion of the capsule to an external receiver.

The following additional Concepts are included as part of the foregoing disclosure.

Concept 1. A capsule device, comprising: a sensor system comprising: a light source; an image sensor for capturing image frames of a scene illuminated by the light source; an archival memory; and a housing adapted to be swallowed, wherein the light source, the image sensor and the archival memory are enclosed in the housing; and a density control means for causing at least two specific gravities of the capsule device for at least two designated regions of gastrointestinal track respectively, wherein each of said at least two specific gravities is selected from a first group consisting of a greater-than-one state and a less-than-one state.

Concept 2. The capsule device of Concept 1, wherein the greater-than-one state correspond to the specific gravity of about 1.1 or larger and the less-than-one state corresponds to the specific gravity of about 0.94 or smaller.

Concept 3. The capsule device of Concept 1, wherein said at least two designated regions of the gastrointestinal track are selected from a second group comprising stomach, ascending colon and descending colon.

Concept 4. The capsule device of Concept 1, wherein said at least two designated regions of the gastrointestinal track correspond to stomach and ascending colon, and wherein the corresponding said at least two specific gravities are the greater-than-one state and the less-than-one state respectively.

Concept 5. The capsule device of Concept 1, wherein said at least two designated regions of the gastrointestinal track correspond to stomach, ascending colon and descending colon, and wherein the corresponding said at least two specific gravities are the greater-than-one state, the less-than-one state and the greater-than-one state respectively.

Concept 6. The capsule device of Concept 1, wherein whether the capsule device is located in or approaching at one of said at least two designated regions of the gastrointestinal track is determined based on: estimated transit time after the capsule device is swallowed; pH values measured at capsule device locations; luminal pressure measured at the capsule device location; identification of image contents based on captured images by the capsule device; motion detection based on the captured images by the capsule device; colonic microflora detected at the capsule device location; or estimation of lumen diameter.

Concept 7. The capsule device of Concept 1, wherein said density control means couples a deformable member to the sensor system, wherein the deformable member contains gas generating material, said density control means causes the deformable member to inflate by causing fluid to enter the deformable member so that the gas generating material generates gas and the capsule device has the specific gravity less than one.

Concept 8. The capsule device of Concept 7, wherein the deformable member is coated with an enteric coating before the capsule device is swallowed to prevent the fluid to enter the deformable member before the capsule device exits stomach.

Concept 9. The capsule device of Concept 7, wherein the deformable member comprises a biodegradable plug, wherein the biodegradable plug becomes separated or partially separated from rest of the deformable member or causes leaks on the deformable member to let the gas and the fluid to leak from the deformable member.

Concept 10. The capsule device of Concept 7, wherein the deformable member is made of a first material which is more permeable to the gas than to the fluid.

Concept 11. The capsule device of Concept 10, wherein the deformable member inflates with the gas and later deflates as the gas diffuses out of the deformable member faster than the fluid diffuses in the deformable member.

Concept 12. The capsule device of Concept 7, wherein after a first period of time since the capsule device reaches the specific gravity less than one, the density control means causes the capsule device to reach the specific gravity greater than one by allowing the fluid to continue to enter the deformable member such that a volume ratio of the gas to the fluid inside the member decreases.

Concept 13. The capsule device of Concept 1, wherein the capsule devise is coated with or made of a second material so that the capsule devise has a reduced friction with body lumen or fluid.

Concept 14. The capsule device of Concept 1, wherein electrical contacts are disposed fixedly on the housing, wherein the electrical contacts are coupled to the archival memory so that an external device is allowed to access image data stored in the archival memory through the electrical contacts.

Concept 15. The capsule device of Concept 14, wherein the electrical contacts include power pins to provide power to the capsule device for data retrieval of image data stored on the archival memory.

Concept 16. The capsule device of Concept 14, wherein inductive powering is used to provide power to the capsule device for data retrieval of image data stored on the archival memory.

Concept 17. The capsule device of Concept 1, wherein the capsule device further comprises: an optical transmitter to transmit an optical signal through a clear window, wherein image data from the archival memory is transmitted to an external optical receiver.

Concept 18. The capsule device of Concept 17, wherein inductive powering is used to provide power to the capsule device for data retrieval of image data stored on the archival memory.

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in claims should not be construed to limit the invention to the specific embodiments disclosed in the specification.

What is claimed is:

1. A capsule endoscope, comprising:

a sensor system comprising a light source, an image sensor for capturing image frames of a scene illuminated by the light source;

a housing adapted for being swallowed, wherein the housing encloses the sensor system; and at least one pouch containing an effervescent, the pouch being attached to the housing and being semi-permeable or porous[, permeable] to body liquid [but not to gas] so that the effervescent is able to generate gas upon contact with the body liquid;

wherein at least the pouch is encapsulated within a dissolvable shell, dome or coating, and wherein specific gravity (SG) of the capsule endoscope is greater than 1 when the pouch is encapsulated within the dissolvable shell, dome or coating and wherein the SG of the capsule endoscope corresponds to a specific gravity of all [the] components of the capsule endoscope collectively together; and wherein [the capsule endoscope] *said at least the pouch* is configured to control [estimated] inflation and deflation periods of [the capsule endoscope] *said at least the pouch* such that the capsule endoscope has the SG of the capsule endoscope greater than 1 for a first period of time, and less than 1 for a second period of time following the first period of time; *and* wherein [the capsule endoscope] *said at least the pouch* is configured to control [estimated] inflation *and deflation periods* of [the capsule endoscope] *said at least the pouch* by [properly] selecting parameters from a parameter group comprising a combination of pouch membrane type and pouch wall thickness *to affect a rate of diffusion of body liquid into the pouch*.

2. The capsule endoscope of claim 1, wherein at least the pouch is encapsulated within an enteric shell, dome or coating.

3. The capsule endoscope of claim 2, wherein the enteric shell, dome or coating is designed to dissolve a pH in range of 5.0-7.4 so that the enteric shell, dome or coating is intended to disintegrate in the small intestine or the cecum.

4. The capsule endoscope of claim 2, wherein the capsule endoscope is configured to cause the specific gravity (SG) of the capsule endoscope drops below 1 in about 2-6 hours after the capsule endoscope is exposed to bodily fluids by swallowing the capsule endoscope.

5. The capsule endoscope of claim 2, wherein the endoscope is configured such that the specific gravity (SG) of the capsule endoscope is more than 1 for more than about six hours after the capsule endoscope is exposed to bodily fluids by swallowing *the capsule endoscope*.

6. The capsule endoscope of claim 2, wherein the pouch has a wall thickness of less than 2 mils for [one] *a first* group of pouch materials or less than 5 mils for [another] *a second* group of pouch materials.

7. The capsule endoscope of claim 2, wherein the pouch is configured such that the specific gravity (SG) of the capsule endoscope is more than 1 for more than 1.5 hours after the pouch is exposed to bodily liquids by swallowing the capsule endoscope.

8. The capsule endoscope of claim 2, wherein the pouch is configured such that the specific gravity (SG) of the capsule endoscope is less than 1 for more than *2 or* 4 hours after the pouch is exposed to bodily liquids by swallowing the capsule endoscope.

9. The capsule endoscope of claim 1, wherein the endoscope is configured such that the specific gravity (SG) of the capsule endoscope drops below 1 in about 2-6 hours after the capsule endoscope is exposed to bodily fluids by swallowing.

10. The capsule endoscope of claim 1, wherein the endoscope is configured such that the specific gravity (SG) of the capsule endoscope is less than 1 for more than about six hours after the capsule endoscope is exposed to bodily fluids by swallowing *the capsule endoscope*.

11. The capsule endoscope of claim 1, wherein the pouch [comprises] *is selected from a set consisting of* polyetherblockamide copolymers, thermoplastic polyurethanes, polyamides, polyamide block copolymers, polyamide elastomers, polyurethanes, polyesters, polyester copolymers, polyamide copolymers, polyurethane copolymers, polyether copolymers, polyesteramides, polyesteramide copolymers, polyvinyl chloride, polyvinyl chloride copolymers, polyvinylidene dichloride, polyvinylidene dichloride copolymers, fluoropolymers, polyvinyl fluoride, polyvinyl fluoride copolymers, polyvinylidene difluoride, polyvinylidene difluoride copolymers, polyvinylpyrrolidone copolymers, [or] *and* polyvinylalcohol copolymers.

12. The capsule endoscope of claim 1, wherein the pouch has a wall thickness of less than 5 mils or less than 10 mils.

13. The capsule endoscope of claim [1] *12*, wherein the pouch water uptake in 12 hours relative to a pouch and effervescent dry weight is less than 200% for [one] *a first* group of pouch materials or 50% for [another] *a second* group of pouch materials.

14. The capsule endoscope of claim 13, wherein the pouch material is selected from a set consisting of polyetherblockamide copolymers, [thermoplastic polyurethanes,] polyamides, polyamide block copolymers, polyamide elastomers, [polyurethanes,] polyesters, polyester copolymers, polyamide copolymers, [polyurethane copolymers,] polyether copolymers, [polyvinyl chloride, polyvinyl chloride copolymers,] polyvinylidene dichloride, polyvinylidene dichloride copolymers, fluoropolymers, polyvinyl fluoride, polyvinyl fluoride copolymers, polyvinylidene difluoride, [or] *and* polyvinylidene difluoride copolymers.

15. The capsule endoscope of claim 1, wherein the Young's modulus of the pouch is:

high enough to create a non-conformal pouch; or low enough to create a slightly conformal pouch, such that the pouch can reach a maximum size 25% above the nominal size with a maximum of 40 mg effervescent.

16. The capsule endoscope of claim 1, wherein the pouch is configured such that the specific gravity (SG) of the capsule endoscope is more than 1 for more than 1.5 hours after the pouch is exposed to bodily liquids by swallowing the capsule endoscope.

17. The capsule endoscope of claim 1, wherein the pouch is configured such that the specific gravity (SG) of the capsule endoscope is less than 1 for more than *2 or* 4 hours after the pouch is exposed to bodily liquids by swallowing the capsule endoscope.

18. The capsule endoscope of claim 1, wherein the pouch is configured such that the specific gravity (SG) is of the capsule endoscope is less than 1 for more than 4 hours but less than 12 hours after the pouch is exposed to bodily liquids by swallowing the capsule endoscope.

19. The capsule endoscope of claim 1, wherein the effervescent is coated.

20. The capsule endoscope of claim [16] *19*, wherein the effervescent coating is an enteric coating designed to a pH in the range of 5.0-7.4 such that the effervescent is intended to react with water after the endoscope has reached the small intestine.

21. The capsule endoscope of claim 1, wherein the pouch further comprises a desiccant.

22. The capsule endoscope of claim 21, wherein the ratio of desiccant to effervescent is 1:10 to 2:1 by weight.

23. The capsule endoscope of claim 1, wherein the pouch has a total exterior surface area of about 300 and 1,000 $mm^2$.

24. The capsule endoscope of claim 23, wherein between about 10 mg and 50 mg of effervescent are contained within the pouch.

25. The capsule endoscope of claim 1, wherein specific gravity (SG) of the capsule endoscope is greater than 1 again for a third period of time following the second period of time after the capsule endoscope is swallowed by a human subject.

26. The capsule endoscope of claim 1, wherein the pouch is configured such that the specific gravity (SG) of the capsule endoscope is less than 1 for more than 4 hours but less than 12 hours after the pouch is exposed to bodily liquids by swallowing the capsule endoscope.

*27. A capsule endoscope, comprising:*

*a sensor system comprising a light source, an image sensor for capturing image frames of a scene illuminated by the light source;*

*a housing adapted for being swallowed, wherein the housing encloses the sensor system; and*

*at least one pouch containing an effervescent, the pouch being attached to the housing and being semi-permeable or porous to body liquid so that the effervescent is able to generate gas upon contact with the body liquid, wherein the effervescent comprises anhydrous acid;*

*wherein said at least the pouch is encapsulated within a dissolvable shell, dome or coating, and wherein specific gravity (SG) of the capsule endoscope is greater than 1 when the pouch is encapsulated within the dissolvable shell, dome or coating and wherein the SG of the capsule endoscope corresponds to a specific gravity of all components of the capsule endoscope collectively together; and*

*wherein said at least the pouch is configured to control inflation and deflation periods of said at least the pouch such that the capsule endoscope has the SG of the capsule endoscope greater than 1 for a first period of time, and less than 1 for a second period of time following the first period of time, and wherein said at least the pouch is configured to control inflation and deflation periods of said at least the pouch by selecting parameters from a parameter group comprising a combination of pouch membrane type and pouch wall thickness to affect a rate of diffusion of body liquid into the pouch.*

* * * * *